United States Patent
Awwad et al.

(10) Patent No.: US 11,928,983 B2
(45) Date of Patent: Mar. 12, 2024

(54) ARTIFICIAL EYE ASSEMBLY FOR STUDYING OCULAR PHARMACOKINETICS

(71) Applicant: Optceutics Limited, London (GB)

(72) Inventors: Sahar Awwad, London (GB); Yann Bouremel, London (GB); Nkiruka Ibeanu, London (GB); Stephen James Brocchini, London (GB); Peng Tee Khaw, London (GB)

(73) Assignee: Optceutics Limited, London (GB)

( * ) Notice: Subject to any disclaimer, the term of this patent is extended or adjusted under 35 U.S.C. 154(b) by 0 days.

(21) Appl. No.: 17/913,085

(22) PCT Filed: Mar. 19, 2021

(86) PCT No.: PCT/GB2021/050686
§ 371 (c)(1),
(2) Date: Sep. 20, 2022

(87) PCT Pub. No.: WO2021/186191
PCT Pub. Date: Sep. 23, 2021

(65) Prior Publication Data
US 2023/0077423 A1 Mar. 16, 2023

(30) Foreign Application Priority Data
Mar. 20, 2020 (GB) ..................... 2004061

(51) Int. Cl.
*G09B 23/28* (2006.01)
*G01F 15/00* (2006.01)
*G01F 15/18* (2006.01)

(52) U.S. Cl.
CPC ......... *G09B 23/285* (2013.01); *G01F 15/005* (2013.01); *G01F 15/18* (2013.01)

(58) Field of Classification Search
CPC ...... G01F 15/005; G01F 15/18; G09B 23/285
(Continued)

(56) References Cited

PUBLICATIONS

Search Report for Patent Appl. No. GB2004061.4 dated Sep. 18, 2020, 3 pages.
(Continued)

*Primary Examiner* — Alexander A Mercado
*Assistant Examiner* — Rodney T Frank
(74) *Attorney, Agent, or Firm* — Maine Cernota & Curran

(57) ABSTRACT

An artificial eye assembly (100) comprising: —an anterior layer (50) comprising an anterior cavity (52); —a flow constricting (40) layer comprising a first aperture (42), and wherein the first aperture (42) is in fluid communication with the anterior cavity (52); —a shaping layer (30) comprising a second aperture and a shaping structure (32), wherein the shaping structure (32) is located within, partially within, or outside of the second aperture, and wherein the shaping structure comprises (32) one or more webs (33), the webs (33) connecting the structure (32) to the rest of the shaping layer (30), and wherein the second aperture is in fluid communication with the first aperture (42); —a flow resistive layer (20) comprising pores, and wherein pores of the layer are in fluid communication with the second aperture; —a posterior layer (10) comprising a posterior cavity (12), and wherein the posterior cavity (12) is in fluid communication with pores of the flow resistive layer (20); —a fluid inlet (13) located in the anterior and/or posterior cavity (12, 52), or located in or adjacent to the second aperture; —a fluid outlet (54) located in the anterior cavity; and —an injection inlet (14) located in the posterior cavity and/or located in the anterior cavity, and wherein the anterior cavity (52) and the posterior cavity (12) are in fluid communication with one another via a fluid path formed through the layers (10, 20, 30, 40 50); and wherein, in use, a fluid introduced under pressure into the assembly via the fluid inlet (13) will flow along the fluid path and exit the assembly via the fluid outlet (54) with a first flow rate.

26 Claims, 10 Drawing Sheets

(58) Field of Classification Search
USPC ........................................................ 73/866.4
See application file for complete search history.

(56) References Cited

PUBLICATIONS

Awwad S et al, The PK-Eye A Novel In Vitro Ocular Flow Model for Use in Preclinical Drug Development, Journal of Pharmaceutical Sciences 104(10): 3330-3342, Jun. 24, 2015, <DOI:10.1002/jps.24480>.
International Search Report and Written Opinion for PCT Appl. No. PCT/GB2021/050686 dated Jun. 24, 2021, 11 pages.
Henein C et al, Hydrodynamics of Intravitreal Injections into Liquid Vitreous Substitutes, Pharmaceutics, 11(8): 317, Aug. 1, 2019, 19 pages, <DOI:10.3390/pharmaceutics11080371>.
Chen Y et al, In Vitro Simulation of In Vivo Pharmacokinetic Model with Intravenous Administration via Flow Rate Modulation, Journal of Pharmacokinetics and Pharmacodynamics, 42(1): 33-43, Oct. 30, 2014, <DOI: 10.1007/S10928-014-9396-7>.
Agrahari V et al, A Comprehensive Insight on Ocular Pharmacokinetics, Drug Delivery And Translational Research, 6(6): 735-754, Oct. 13, 2016, <Doi: 10.1007/S13346-016-0339-2>.

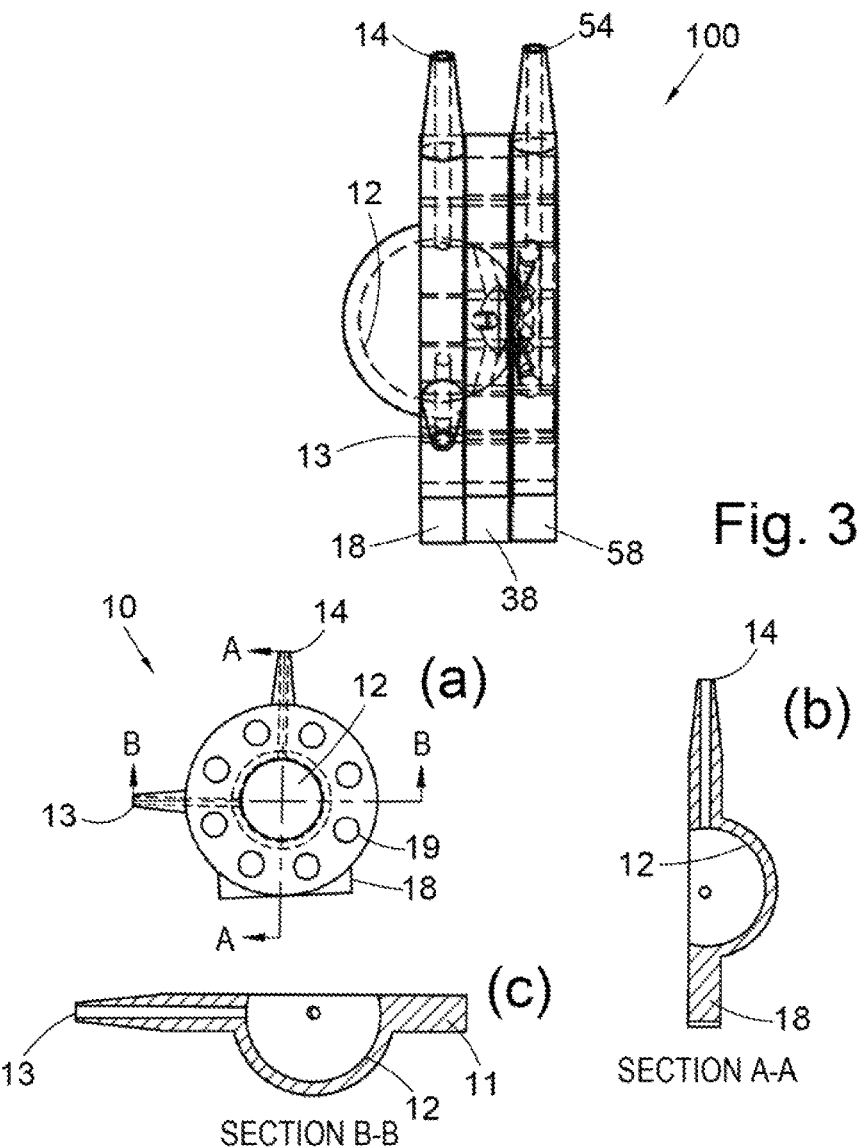
Fig. 3
Fig. 4
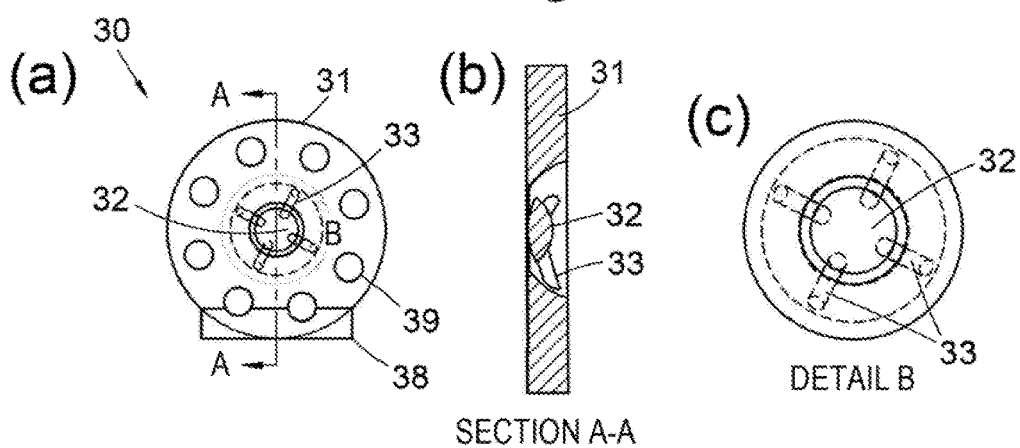
Fig. 5

ARTIFICIAL EYE ASSEMBLY FOR STUDYING OCULAR PHARMACOKINETICS

RELATED APPLICATIONS

This application is a national phase application filed under 35 USC § 371 of PCT Application No. PCT/GB2021/050686 with an International filing date of Mar. 19, 2021, which claims priority of GB Patent Application 2004061.4 filed Mar. 20, 2020. Each of these applications is herein incorporated by reference in its entirety for all purposes.

FIELD OF THE INVENTION

This invention relates to an artificial eye assembly, though not exclusively, the invention relates to an artificial eye assembly made up of layers; as well as kits, method and uses of the same.

BACKGROUND OF THE INVENTION

Age-related macular degeneration, glaucoma and diabetic retinopathy are major diseases that cause blindness. Treatment of these, and other eye diseases, involve the direct intravitreal injection of medicine into the back of the eye (i.e. the posterior segment/cavity of the eye) to achieve a high and reproducible dose. Since many blinding conditions are chronic, patients often require intravitreal injections over many years. Currently, an injection of a drug is required every two to three months to treat many of these conditions. A great deal of research is being conducted so that less frequent injections are required (e.g. once every 6 months).

Assessment of protein-based medicines in animals is very difficult and prohibitively expensive in this area. That is, animal models (i) vary in their predictive capacity due to anti-drug antibodies, (ii) have anatomic and aqueous outflow differences in the eye, (iii) are challenging to evaluate over time and (iv) are extremely expensive and time consuming to conduct.

In particular, anti-drug antibody formation is problematic. This is because human therapeutic proteins will generate anti-drug antibodies in animal models, which result in rapid clearance of the candidate drug. This makes allometric modelling in animals very difficult/inaccurate when looking to develop longer-acting treatment formulations. Therefore, formation of anti-drug antibodies is an almost intractable problem for industry in this area. While there are a few in vitro models that have been described for ocular pharmacokinetics, none are predictive of the pharmacokinetic properties of intraocular therapeutics.

There remains a need in the art for improved solutions for studying treatments of the eye, and in particular for studying treatments of the human eye.

SUMMARY OF THE INVENTION

In a first aspect of the invention, there is provided an artificial eye assembly comprising: an anterior layer comprising an anterior cavity;
a flow constricting layer comprising a first aperture, and wherein the first aperture is in fluid communication with the anterior cavity;
a shaping layer comprising a second aperture and a shaping structure, wherein the shaping structure is located within, partially within, or outside of the second aperture, and wherein the shaping structure comprises one or more webs, the webs connecting the structure to the rest of the shaping layer, and wherein the second aperture is in fluid communication with the first aperture;
a flow resistive layer comprising pores, and wherein pores of the layer are in fluid communication with the second aperture;
a posterior layer comprising a posterior cavity, and wherein the posterior cavity is in fluid communication with pores of the flow resistive layer;
a fluid inlet located in the posterior cavity, or located in or adjacent to the second aperture; a fluid outlet located in the anterior cavity; and
an injection inlet located in the posterior cavity and/or located in the anterior cavity,
and wherein the anterior cavity and the posterior cavity are in fluid communication with one another via a fluid path formed through the layers;
and wherein, in use, a fluid introduced under pressure into the assembly via the fluid inlet will flow along the fluid path and exit the assembly via the fluid outlet with a first flow rate.

The present invention provides an artificial eye, which at the least enables the effective study of ocular pharmacokinetics. The invention allows for the compartmentalised and automated in vitro modelling of the human eye, which can be used to estimate ocular drug kinetics under the influence of various ocular parameters and physiological conditions. The invention may also provide pressurised multi-modular chambers. The chambers broadly mimic the various regions of the eye. The multi-modular layers forming chambers, may therefore be changed on an individual basis to suit experimental need. In addition, the problem of anti-drug antibody formation is avoided due to the synthetic nature of the eye assembly.

The assembly of the present invention for example may provide ciliary flow rates and characteristics similar to a living human eye. Each chamber of the artificial eye may for example be pressurised at different levels to reproduce relative flow rates through the eye, which may simulate different wake and sleep cycles. The simulated chambers of the eye are in effect separated by porous membranes, which can be changed to model healthy and diseased eye conditions. In addition, for example, the posterior cavity of the assembly may be filled with different vitreous substitutes to mimic (i) vitrectomised, (ii) non-vitrectomised and (iii) ageing eyes. The effect of the vitreous substitutes can be used to further explore drug kinetics and drug distribution under the influence of eye movements (saccades) and convection. As such, the nature and structure of the invention allows for a modular eye assembly where various parts of the assembly can be tailored to simulate healthy and diseased eyes as well as drug transfer through the various parts of the eye.

In an embodiment, the shaping layer is absent, and wherein pores of the flow resistive layer are in fluid communication with the first aperture; or the flow constricting layer is absent, and wherein the second aperture is in fluid communication with the anterior cavity. In some circumstances, it may be useful to model a system where one of these layers is not present in the assembly; for example, to assess the impact of the missing part in a comparative experiment.

In an embodiment, the posterior cavity comprises one or more cavity apertures, and the assembly further comprises:

a second flow resistive layer comprising pores, and wherein pores of the second flow resistive layer are in fluid communication with the one or more cavity apertures;

an outlet layer comprising a posterior outlet, and wherein the posterior outlet is in fluid communication with pores of the second flow resistive layer; and a flow balancing conduit which is in fluid communication with the posterior outlet, and wherein the posterior cavity and the flow balancing conduit are in fluid communication with one another via a second fluid path, and wherein, in use, the fluid introduced under pressure into the assembly via the fluid inlet will also flow along the second fluid path and exit the assembly via the posterior outlet with a second flow rate; and wherein a flow balancing fluid will pass through the flow balancing conduit with a third flow rate, such that the sum of the second and third flow rates will be equal to the first flow rate. This arrangement can be used to better model the human eye, and so be used to assess the movement of drugs through both the front and back of the eye.

In an embodiment, the anterior cavity comprises a third aperture and the assembly further comprises:

an elastic layer sealing the third aperture; and a retaining layer which secures the elastic layer in place and which comprises a purse limiting means, and wherein, in use, the fluid introduced under pressure into the assembly will cause the elastic layer to purse, and wherein the purse limiting means limits the degree of pursing. This system can be used to better model the eye, to create a region that better matches the cornea of the human eye.

In an embodiment, the purse limiting means is a fourth aperture in the retaining layer, wherein the elastic layer is sized to cover the fourth aperture. The fourth aperture, can be tailored to create the desired level of pursing.

In an embodiment, the assembly further comprises a temperature regulating means to control or maintain the temperature within the assembly, or to induce a temperature difference within the assembly. Such a temperature difference can be used to generate convection currents within regions of the artificial eye. In an embodiment, the temperature regulating means controls or maintains the temperature within one or more layers within the assembly.

In an embodiment, the temperature regulating means comprises a source of radiation. In an embodiment the source of radiation is a heating lamp, such as an UV or IR heating lamp. In an embodiment the source of radiation is a vivarium lamp.

In an embodiment, the temperature regulating means comprises a volume for containing a thermally regulated fluid, and a heat or cooling means to adjust the temperature of the thermally regulated fluid when present, wherein the volume is in thermal contact with, and/or encompasses, one or more of:

the outlet layer;

the posterior layer; and the shaping layer, and wherein, in use, the thermally regulated fluid is introduced into the volume and is maintained at a constant temperature, thereby transferring heat to, or from, the thermally contacted layers.

In an embodiment, the thermally regulated fluid may enter the volume via a volume feeding inlet. In an embodiment, the volume encompasses and/or extends through the outlet layer and the posterior layer, and abuts the shaping layer. In an embodiment, the fluid inlet feeds into the shaping layer and the fluid inlet is in thermal contact with the volume. In an embodiment, when the fluid inlet is located in, or adjacent to, the second aperture, and the shaping layer is in thermal contact with the volume, then the fluid passing through the inlet is arranged to flow in a circuitous fluid path through the shaping layer. In an embodiment, in use, the temperature regulating means causes thermal convection currents in a volume of fluid situated between the second aperture and the anterior cavity. In an embodiment, when in use the thermally regulated fluid is 0.1, 0.2, 0.25, 0.3, 0.4, 0.5, 0.6, 0.75, 0.8, 0.9, 1.0, 1.25, 1.5, 2.0 or 2.5'C above, or below, room temperature. In an embodiment, the temperature of the thermally regulated fluid is 37.5° C. In an embodiment, the thermally regulated fluid is water or oil. In an embodiment, the assembly rests in a thermally regulated bath. It is useful to be able to control the temperature of the eye assembly. This can be used to create convection currents in a portion of the eye (e.g. within a fluid held in the anterior cavity); or to ensure that the transport kinetics are controlled with respect to a constant temperature. As such, the eye assembly as a whole can be maintained at a certain temperature, or if heating is done within the eye assembly, certain regions of the eye assembly may be heated or cooled selectively.

In an embodiment, the assembly further comprises a pump to pump the fluid under pressure through the assembly via the first fluid path, and also via the second fluid path when the second fluid path is present. In an embodiment, capillary tubing is in fluid communication with any one of the inlets or outlets of the assembly to increase the pressure within the assembly or parts of the assembly. In an embodiment, the capillary tubing has an internal diameter (lumen) of 0.03 to 5.0 mm, 0.5 to 3.0 mm, or 0.5 to 2.5 mm. In an embodiment, the pump is a peristaltic pump. In an embodiment, the fluid is pumped at a rate of 0.1 to 10.0 µL/min, 0.5 to 5.0 µL/min, 1 to 3.0 µL/min, or 1.5 to 2.5 µL/min. In an embodiment, the fluid is pumped at a pressure of 0 to 10 mmHg, 0.1 to 10 mmHg, 1 to 15 mmHg, 10 to 30 mmHg, 30 to 50 mmHg, 50 to 1000 mmHg, 100 to 600 mmHg, 200 to 500 mmHg, or 300 to 400 mmHg. In an embodiment, the fluid is pumped at a pressure of less than 1 mmHg, 5 mmHg, 10 mmHg, 30 mmHg, 50 mmHg, 100 mmHg, 200 mmHg, 300 mmHg, 400 mmHg, 500 mmHg, 600 mmHg, 700 mmHg, 800 mmHg, 900 mmHg, or 1000 mmHg. In an embodiment, the fluid is pumped at a pressure of more than 1 mmHg, 5 mmHg, 10 mmHg, 30 mmHg, 50 mmHg, 100 mmHg, 200 mmHg, 300 mmHg, 400 mmHg, 500 mmHg, 600 mmHg, 700 mmHg, 800 mmHg, 900 mmHg, or 1000 mmHg. In an embodiment, the fluid conduits are microfluidic conduits. In an embodiment, the fluid is laminar. It can be useful to be able to control the rate of fluid movement through the various layers of the eye assembly. This can be done by increasing (or decreasing) the applied pressure using a pump. In this way volumes of fluid, usually small volumes, can be pushed out of the various fluid outlets.

In an embodiment, in use, a cavity volume between the flow resistive layer and the posterior cavity is filled with a fluid permeable packing material. In an embodiment, the fluid permeable packing material comprises a polymer or polymeric substance, wherein the dynamic viscosity of the polymer is 0.0001 to 2.0 Pa·s. In an embodiment, the fluid permeable packing material may be, but is not limited to, hyaluronic acid, collagen, agar, silicon oil, chitosan, alginates, or polysaccharides. It can be useful to control the nature of the material between the flow resistive layer and the posterior cavity. Broadly, this filled volume corresponds to the vitreous body of the human or animal eye. By controlling the nature of the material in this volume, the artificial eye can for example be made to better model/mimic healthy or diseased eye conditions.

In an embodiment, one or more of the layers of the assembly are formed together as a single layer, and optionally may be 3D printed. In an embodiment, one (or more) of the intermediate layers may be omitted from the assembly. In an embodiment, the eye assembly as a whole is 3D printed. It can be convenient to 3D print the various components, layers or the artificial eye as a whole. In an embodiment, one or more of the layers of the assembly are elastic and/or biocompatible.

In an embodiment, the layers are modular units and may be reversibly, or non-reversibly, combined to form the assembly. In an embodiment, one (or more) of the intermediate layers may be omitted from the assembly. In an embodiment, the assembly is pressure tight. In an embodiment, the assembly is fluid tight. In some situations, it can be convenient to allow the artificial eye to be disassembled and reassembled, perhaps interchanging parts/layers. Additionally, a non-reversibly combined eye assembly could be made for a series of experiments, where it is convenient to minimise the number of variables.

In an embodiment, the anterior cavity, posterior cavity, first aperture, shaping structure are substantially shaped and/or sized to replicate corresponding parts of the human eye. Of course, animal eyes can be modelled in a corresponding way by taking account of the anatomical differences. Generally, while modelling animal eyes is considered, for simplicity references to only human eyes are generally made here. In an embodiment, the anterior cavity is substantially shaped and/or sized to replicate the anterior chamber of the human eye. In an embodiment, the posterior cavity is substantially shaped and/or sized to replicate the posterior chamber of the human eye. In an embodiment, the flow constricting layer is substantially shaped and/or sized to replicate the iris of the human eye. In an embodiment, the first aperture is substantially shaped and/or sized to replicate the pupil of the human eye. In an embodiment, the shaping layer is substantially shaped and/or sized to replicate the lens structure of the human eye. In an embodiment, the shaping structure is shaped and/or sized to replicate the lens of the human eye. In an embodiment, the shaping structure is shaped and/or sized to shape the fluid permeable packing material to replicate the vitreous humour of the human eye. In an embodiment, the fluid permeable packing material is substantially shaped and/or sized to replicate the vitreous humour of the human eye. In an embodiment, the various layers/parts are shaped and/or sized to replicate the human eye at different stages of development and/or of ageing. In an embodiment, the various layers/parts are shaped and/or sized to replicate the human eye in a diseased state or in different stages of a disease. It is advantageous in many cases for the various parts/layers of the artificial eye to replicate or substantially mimic the corresponding parts of the human eye.

In an embodiment, one or more layers comprise cooperating projections and/or cooperating recesses/holes that permit alignment of the layers during assembly of the artificial eye assembly. In an embodiment, the shaping layer comprises cooperating projections and the anterior layer comprises cooperating recesses/holes that permit alignment of the layers during assembly of the artificial eye assembly, the projections fitting into the recesses/holes. In an embodiment, one or more layers comprise fixing holes to permit the assembly to be pinned/screwed together. In an embodiment, the fixing holes are axially aligned through each layer. In an embodiment, the fixing holes are threaded to match a cooperating screw. In an embodiment, the one or more layers comprise one or more screw holes, the holes passing through the layers. In an embodiment, the layer comprises 1 to 20, 4 to 12, or 6 to 20 screw holes. In an embodiment, the diameter of the screw holes is 1 to 10 mm, 5 to 8 mm, 6 to 7 mm. In an embodiment, the screw holes are 6.5 mm to accommodate M6 screws. In an embodiment, the one or more layers with screw holes are independently selected from: the retaining layer, the anterior layer, the flow constricting layer, the shaping layer, the flow resistive layer, the posterior layer, the second flow resistive layer, and the outlet layer. In an embodiment, the screw holes are axially aligned through each layer. In an embodiment, the screw holes are threaded to match a cooperating screw. It is advantageous to allow the eye assembly to be assembled in an efficient manner, and having cooperating parts can be used to ensure the parts are aligned correctly before fixing them in place. Likewise, having a series of holes which together form a channel that can cooperate with a single fixing screw is a convenient mode of assembly; simplifying the process and this can help to avoid the misalignment of parts/layers.

In an embodiment, the posterior cavity is fed by a side-mounted or top-mounted fluid inlet. In an embodiment, the fluid inlet feeds into the side of the central bowl-like bore of the shaping layer. In an embodiment, the fluid inlet is located in, or adjacent to, the second aperture of the shaping layer. In an embodiment, the fluid inlet has an internal diameter (lumen) of 0.03 to 5 mm, 0.5 to 3 mm, or 1 to 2.5 mm. In an embodiment, the cavity apertures are radially arranged. In an embodiment, the cavity apertures have an internal diameter (lumen) of 0.03 to 4 mm, 0.5 to 3 mm, or 0.1 to 2 mm. In an embodiment, the cavity apertures comprise a mesh-like structure. It can be advantageous to have these radially arranged holes as they better mimic the trabecular meshwork of the eye. In an embodiment, a fluid may be injected into the posterior cavity via a side-mounted or top-mounted injection inlet. In an embodiment, the injection inlet feeds into the side of the central bowl-like bore of the shaping layer. In an embodiment, the injection inlet is located in, or adjacent to, the second aperture of the shaping layer. In an embodiment, the injection inlet has an internal diameter (lumen) of 0.03 to 5 mm, 0.5 to 3 mm, or 1 to 2.5 mm. In an embodiment, the injection inlet is adapted to fit a needle size of 7 to 33 G. In an embodiment, the injection inlet is sealed by a valve. Depending on need, it can be convenient to add fluid (or fluid containing a drug or active agent) to the posterior cavity or nearer the lens body. This is because drugs or fluids containing drugs can be added to the corresponding parts of the human eye when they are being treated by injection. Therefore, having access to these corresponding regions in the eye assembly can be useful in modelling treatment and drug kinetics. In an embodiment, the fluid outlet is centrally located in the anterior cavity. Advantageously, this fluid outlet can be seen as corresponding to the aqueous vein structure in the human eye. In an embodiment, the fluid outlet has an internal diameter (lumen) of 0.03 to 5 mm, 0.5 to 3 mm, or 1 to 2.5 mm. In an embodiment, the cavity aperture of the posterior layer has an aperture diameter of 1 to 23 mm, 3 to 7 mm, or 4 to 6 mm. In an embodiment, the posterior outlet is centrally located with respect to the posterior cavity. Advantageously, being able to model fluid moving out of the eye via the back area is also useful. The fluid flow out of the back of the eye can mimic the retinal-choroid-sclera pathway. It can be important to model this pathway since it was found that for eight beta-blockers across the human scleral choroidal retinal pigment epithelium, the permeability ranges from $1.34 \times 10^{-6}$ to $6.03 \times 10^{-6}$ cm/s denoting a variation with a ratio of approximately 1:5. In an embodiment, the flow balancing conduit has an internal diameter (lumen) of 0.03 to 5 mm, 0.5 to 3 mm, or 1 to 2.5 mm. In an embodiment, the injection inlet is arranged orthogonally to the fluid inlet.

In an embodiment, the injection inlet is arranged orthogonally or parallel to the fluid outlet. In an embodiment, the injection inlet is arranged orthogonally to the fluid inlet and fluid outlet. In an embodiment, the fluid inlet is arranged orthogonally to the fluid outlet. In an embodiment, the posterior outlet is arranged orthogonally to the flow balancing conduit. Advantageously, inlets/outlets arranged orthogonally with respect to each other can permit the convenient attachment of the pipework to the various inlets/outlets. In an embodiment, at least two of the first, second, third and fourth apertures are axially aligned. In an embodiment, the first, second, third and fourth apertures are axially aligned. Aligning the apertures better mimics the structure of the human eye. In an embodiment, the first aperture has a diameter of 1 to 15 mm, 2 to 10 mm, or 3 to 5 mm. In an embodiment, the second aperture has a widest diameter of 1 to 15 mm, 2 to 10 mm, or 3 to 5 mm. In an embodiment, the third aperture has a diameter of 2 to 23 mm, 5 to 12 mm, or 6 to 8 mm. In an embodiment, the fourth aperture has a diameter of 2 to 20 mm, 5 to 12 mm, or 6 to 7 mm. In an embodiment, the posterior outlet is centrally located in the posterior cavity.

In an embodiment, the assembly further comprises a means to rock, twist, or agitate the assembly. In an embodiment, the assembly comprises a base portion or fits within a removable stand. In an embodiment, the removable stand is capable of rocking, twisting (e.g. to spin or oscillate the eye assembly on a rotational axis) or agitating the eye assembly. In an embodiment, the assembly comprises an integrated base portion supporting the substantially circular layers. A flattened base area allows the eye assembly to stand upright. Rocking, twisting or agitation of the eye assembly permits the ability to better model eye movements (saccades) in the human eye. In an embodiment, the removable stand is capable of supporting more than one eye assembly.

In an embodiment, the anterior layer is substantially circular with a diameter of 10 to 70 mm, 30 to 60 mm, or 45 to 55 mm. In an embodiment, the anterior layer has a thickness of 1 to 12 mm, 4 to 10 mm, or 5 to 7 mm. In an embodiment, the anterior layer is made of 3D printed resin such as photopolymer resin, examples of current commercial ones available are draft resin, tough 1500 resin, black resin, grey resin, clear resin, white resin, tough resin, flexible resin, elastic resin, durable resin, rigid resin, high-temp resin, grey pro resin, colour base resin, castable resin, castable wax resin, dental SG resin, dental model resin, dental LT clear resin, all available from Formlabs (as of 1 Mar. 2020). In an embodiment, the eye assembly comprises a viewing window. In an embodiment, one or more layers comprise, or consist of a clear material. In an embodiment, one or more layers comprise, or consist of a clear resin. In an embodiment, the anterior layer comprises a viewing window. In an embodiment, the anterior layer comprises, or consists of, a clear material. In an embodiment, the anterior layer comprises, or consists of, a clear resin. It can be advantageous to have a way to see into the interior of the eye assembly. In that way visual inspection and/or measurements can be taken. For example a dye could be used to visualise fluid movement within the eye. Instruments like UV or IR detectors could be used to measure the presence/concentration of an UV/IR responsive material within the eye, such as the clearance of a drug having a chromophore. The window may for example be adapted to accommodate a camera or instrument. In an embodiment, the anterior layer is made of a metal or alloy, such as stainless steel. In an embodiment, the anterior cavity has a volume of 0.1 to 5.0 ml, 0.2 to 3.0 ml, or 0.5 to 1.0 ml. In an embodiment, the anterior cavity is bowl shaped with a depth of 0.5 to 6.0 mm, 1 to 4.0 mm, or 2.0 to 3.0 mm. In an embodiment, the anterior cavity is bowl shaped with a diameter of 8 to 20 mm, 12 to 18 mm, or 14 to 16 mm. In an embodiment, the anterior cavity comprises a plurality of drainage holes in fluid communication with the fluid outlet. In an embodiment, the plurality of drainage holes number 2 to 20, 4 to 12, or 6 to 10 holes. In an embodiment, the drainage holes are radially arranged. In an embodiment, the drainage holes comprise a mesh-like structure. It can be advantageous to have these radially arranged holes as they better mimic the trabecular meshwork of the eye. In an embodiment, the drainage holes feed a torus shaped conduit, the torus shaped conduit in fluid communication with the fluid outlet. In an embodiment, the drainage holes feed a torus shaped conduit, the torus shaped conduit in fluid communication with a vertically arranged fluid outlet. The torus-like structure better mimics the Schlemm's canal of the human eye.

In an embodiment, the flow constricting layer is circular with a diameter of 10 to 70 mm, 30 to 60 mm, or 45 to 55 mm. In an embodiment, the flow constricting layer has a thickness of 0.1 to 10 mm, 0.2 to 0.6 mm, or 0.3 to 0.5 mm. In an embodiment, the flow constricting layer is made of material selected from any one of silicone, reconstituted cellulose, regenerated cellulose, cellulose ester (e.g. cellulose acetate and nitrate), polyethersulfone (hydrophobic and hydrophilic), polycarbonate, composite regenerated cellulose, polytetrafluoroethylene and polyvinylidene difluoride. In an embodiment, the first aperture is centrally located within the flow constricting layer. In an embodiment, the first aperture has a diameter of 1 to 15 mm, 2 to 10 mm, or 3 to 5 mm. In an embodiment, the flow constricting layer is capable of binding to a drug or active agent. The flow constricting layer provides a mechanic to control the flow of fluid through the artificial eye. The flow of liquid only being able to pass through the aperture, the aperture corresponding to the pupil of the human eye. The surrounding parts of the assembly likewise corresponding to the iris of the human eye.

In an embodiment, the shaping layer is substantially circular with a diameter of 10 to 70 mm, 30 to 60 mm, or 45 to 55 mm. In an embodiment, the shaping layer has a thickness of 2 to 15 mm, 4 to 10 mm, or 5 to 7 mm. In an embodiment, the shaping layer is made of 3D printed resin such as photopolymer resin, examples of current commercial ones available are draft resin, tough 1500 resin, black resin, grey resin, clear resin, white resin, tough resin, flexible resin, elastic resin, durable resin, rigid resin, high-temp resin, grey pro resin, colour base resin, castable resin, castable wax resin, dental SG resin, dental model resin, dental LT clear resin, all available from Formlabs (as of 1 Mar. 2020). In an embodiment, the shaping layer is made of a metal or alloy, such as stainless steel. In an embodiment, the shaping layer has a bowl-shaped bore through its centre defining a second aperture, which has a depth of 2 to 15 mm, 4 to 10 mm, or 5 to 7 mm and a diameter of 10 to 30 mm, 15 to 25 mm, or 20 to 22 mm. In an embodiment, the shaping structure has a radius of curvature for the anterior-facing surface of 7 to 14 mm, 8 to 12 mm, or 9 to 11 mm. In an embodiment, the shaping structure has a radius of curvature for the posterior-facing surface of 3 to 10 mm, 4 to 8 mm, or 5 to 7 mm. In an embodiment, the shaping structure has apexes of the anterior-facing and posterior-facing surfaces of 5 to 15 mm, 7 to 12 mm, or 8 to 10 mm apart. In an embodiment, the shaping structure has a volume of 0.01 to 5.0 ml, 1.0 to 3.0 ml, or 1.5 to 2.0 ml. In an embodiment, the shaping layer has a thickness of 2 to 12 mm, 4 to 10 mm, or 5 to 7 mm. In an embodiment, the shaping structure is attached to the rest of the shaping layer by 1 to 20, 4 to 10, or 6 to 8 webs.

In an embodiment, the second aperture comprises a plurality of inlet holes in fluid communication with the fluid inlet. In an embodiment, the plurality of inlet holes in fluid communication with the fluid inlet are 2 to 20, 6 to 16, or 10 to 14 in number. In an embodiment, the one or more inlet holes feed a surrounding conduit, wherein the surrounding conduit is in fluid communication with the fluid inlet. In an embodiment, the one or more inlet holes have an internal diameter (lumen) of 0.03 to 5 mm, 0.5 to 3 mm, or 0.5 to 2.5 mm. In an embodiment, fluid may enter the central bore of the shaping layer (i.e. second aperture), via a top-mounted fluid inlet, via a circuitous route. In an embodiment, the circuitous route comprises a spiral. In an embodiment, the circuitous route bifurcates forming a square-shaped loop located within the plate body region of the shaping layer. In an embodiment, the square-shaped loop comprises 2 to 20, 8 to 16, or 10 to 14 spaced apart conduits that feed into the central bore of the plate body region of the shaping layer. It can be advantageous to add fluid to the area in/around the shaping layer, a layer that corresponds to the lens area of the human eye. Having various holes allows the fluid to enter the area evenly. A conduit with a circuitous path (e.g. a spiralling tube) allows for thermal equilibration of the fluid traveling in the conduit before it enters the area in/around the shaping body.

In an embodiment, the shaping layer comprises 2 to 16, 4 to 12, or 6 to 10 spaced apart peg-like protrusions, which are arranged to cooperate with complementary holes/recesses in the anterior layer. In an embodiment, the protrusions are arranged to pass through complementary holes in the flow constricting layer. Advantageously, these parts allow the eye assembly to be more conveniently assembled. In an embodiment, the shaping layer is capable of binding to a drug or active agent. In an embodiment, the shaping structure layer comprises a drug-binding material selected from any one of silicone, reconstituted cellulose, regenerated cellulose, cellulose ester (e.g. cellulose acetate and nitrate), polyethersulfone (hydrophobic and hydrophilic), polycarbonate, composite regenerated cellulose, polytetrafluoroethylene and polyvinylidene difluoride. Advantageously, as mentioned here (and later in respect of other parts/layers) it may be useful if the part/layer is capable of binding to a drug or active agent. This is because this binding may be occurring naturally in the human eye in the corresponding parts of the human body. Therefore, being able to model this drug binding/retaining property in the artificial eye is useful.

In an embodiment, the flow resistive layer comprises, or consists of, a membrane, the membrane comprising pores. In an embodiment, the membrane contacts the shaping structure and is shaped by the shaping structure. In an embodiment, in use, the membrane contacts the shaping structure and is shaped by the shaping structure under pressure, when fluid passes through the eye assembly. In an embodiment, the flow resistive layer is circular with a diameter of 1 to 40 mm, 15 to 35 mm, or 20 to 30 mm. In an embodiment, the flow resistive layer has a thickness of 0.02 to 10 mm, 0.2 to 0.6 mm, or 0.3 to 0.5 mm. In an embodiment, the portion of the flow resistive layer (or membrane within a flow resistive layer) which in use is in contact with a fluid, has a diameter of 0.02 to 30 mm, 5 to 20 mm, or 7 to 10 mm. In an embodiment, the membrane is centrally located within the flow resistive layer. In an embodiment, the membrane is made of material selected from any one of silicone, reconstituted cellulose, regenerated cellulose, cellulose ester (e.g. cellulose acetate and nitrate), polyethersulfone (hydrophobic and hydrophilic), polycarbonate, composite regenerated cellulose, polytetrafluoroethylene and polyvinylidene difluoride. In an embodiment, the pore sizes of the membrane are selected from any one of 10 angstrom to 5 μm. In an embodiment, the flow resistive layer has a molecular weight cut off of 3.5 to 1000 kDa, 200 to 500 kDa, or 250 to 350 kDa. In an embodiment, the flow resistive layer is configured to allow a flow rate of 0.1 to 104 μL/min, 0.5 to 64 μL/min, or 1.5 to 4 μL/min when the appropriate pressure is applied. In an embodiment, the flow resistive layer is capable of binding to a drug or active agent. The flow resistive layer provides one of the main mechanics to control the flow of fluid through the artificial eye. In effect the more porous the membrane (be it increased pore size, increased pore density, or larger area having the pores) the greater the flow of the fluid through the flow resistive layer (where all other physical parameters are constant). The same is true of the second flow resistive layer.

In an embodiment, the posterior layer is substantially circular with a diameter of 10 to 70 mm, 30 to 60 mm, or 45 to 55 mm. In an embodiment, the posterior layer has a thickness of 1 to 12 mm, 4 to 10 mm, or 5 to 7 mm. In an embodiment, the posterior layer is made of 3D printed resin. In an embodiment, the posterior layer is made of a metal or alloy, such as stainless steel. In an embodiment, the posterior cavity has a volume of 1 to 8 ml, 3 to 6 ml, or 4 to 5 ml. In an embodiment, the posterior cavity is bowl-shaped with a depth of 5 to 30 mm, 10 to 20 mm, or 12 to 16 mm. In an embodiment, the posterior cavity is bowl-shaped with a diameter of 10 to 40 mm, 15 to 30 mm, or 20 to 25 mm. In an embodiment, the posterior cavity comprises a centrally located cavity aperture that passes through the bowl-shaped structure. In an embodiment, the posterior cavity aperture has an aperture diameter of 0.02 to 10 mm, 3 to 8 mm, or 4 to 6 mm. In an embodiment, the posterior cavity comprises 2 to 30, 8 to 20, or 12 to 14 substantially evenly spaced apertures. In an embodiment, the posterior cavity resembles the bowl region of a colander. A colander-like shape provides more holes and so provides a more even drainage area and a larger contact area with the vitreous.

In an embodiment, the second flow resistive layer comprises, or consists of, a membrane, the membrane comprising pores. In an embodiment, the membrane in use is located between the posterior layer and the outlet layer. In an embodiment, the second flow resistive layer is circular with a diameter of 1 to 70 mm, 15 to 35 mm, or 20 to 30 mm. In an embodiment, the second flow resistive layer has a thickness of 0.02 to 10 mm, 0.2 to 0.6 mm, or 0.3 to 0.5 mm. In an embodiment, the portion of the second flow resistive layer (or membrane within a second flow resistive layer) which in use is in contact with a fluid, has a diameter of 0.02 to 30 mm, 5 to 20 mm, or 7 to 10 mm. In an embodiment, the membrane is centrally located within the second flow resistive layer. In an embodiment, the membrane is made of a martial selected from anyone of silicone, reconstituted cellulose, regenerated cellulose, cellulose ester (e.g. cellulose acetate and nitrate), polyethersulfone (hydrophobic and hydrophilic), polycarbonate, composite regenerated cellulose, polytetrafluoroethylene and polyvinylidene difluoride.

In an embodiment, the pore sizes of the membrane are selected from 1 nm to 10 nm. In an embodiment, the second flow resistive layer has a molecular weight cut off of 3.5 to 20 kDa, 10 to 16 kDa, or 12 to 14 kDa. In an embodiment, the second flow resistive layer allows a flow rate of 0.01 to 10 µL/min, 0.5 to 2 µL/min, or 0.75 to 1 µL/min when the appropriate pressure is applied. In an embodiment, the second flow resistive layer is capable of binding to a drug or active agent.

In an embodiment, the flow rate permitted by the flow resistive layer is greater, equal or less than the flow rate permitted by the second flow resistive layer under the same physical conditions. In an embodiment, the flow rate permitted by the flow resistive layer is greater than the flow rate permitted by the second flow resistive layer under the same physical conditions. In an embodiment, the flow rate permitted by the second flow resistive layer is at least 1, 5, 10, 20, 25, 50, 75, 80, 90, 95 or 98% lower than the flow rate permitted by the (first) flow resistive layer under the identical physical conditions (such as pressure, surface area and temperature). It can be advantageous to be able to control the rate of fluid leaving the artificial eye from the front verses the back of the eye. This can be done by changing the effective relative porosity of the (first) flow resistive layer as compared to the second flow resistive layer.

In an embodiment, the outlet layer is substantially circular with a diameter of 10 to 70 mm, 30 to 60 mm, or 45 to 55 mm. In an embodiment, the outlet layer has a thickness of 0.1 to 5 mm, 2 to 4 mm, or 2.5 to 3.5 mm. In an embodiment, the outlet layer is made of 3D printed resin. In an embodiment, the outlet layer is made of a metal or alloy, such as stainless steel. In an embodiment, the outlet layer comprises a mating cavity, the mating cavity shaped to mate with the posterior layer. In an embodiment, the mating cavity has a volume of 1.1 to 9.0 ml, 3.0 to 7.0 ml, or 5.0 to 6.0 ml. In an embodiment, the mating cavity has a larger diameter than the posterior cavity. In an embodiment, the mating cavity is bowl-shaped with a depth of 5.1 to 35 mm, 11 to 25 mm, or 13 to 18 mm. In an embodiment, the mating cavity is bowl shaped with a diameter of 11 to 45 mm, 16 to 35 mm, or 21 to 26 mm. In an embodiment, the wall of the mating cavity has a thickness of 0.1 to 12 mm, 4 to 10 mm, or 5 to 7 mm. In an embodiment, the posterior outlet has an internal diameter (lumen) of 0.03 to 5 mm, 0.5 to 3 mm, or 0.5 to 2.5 mm. In an embodiment, the flow balancing conduit is arranged orthogonally to the posterior outlet. In an embodiment, the flow balancing conduit has an internal diameter (lumen) of 0.03 to 5 mm, 0.5 to 3 mm, or 0.5 to 2.5 mm. In an embodiment, the third aperture is centrally located within the anterior cavity.

In an embodiment, the elastic layer comprises, or consists of, silicone. In an embodiment, the elastic layer is clear. In an embodiment, the elastic layer impermeable. In an embodiment, the elastic layer has Shore Hardness A. In an embodiment, the elastic layer is circular with a diameter of 1 to 40 mm, 15 to 35 mm, or 20 to 25 mm. In an embodiment, the elastic layer has a thickness of 0.1 to 10 mm, 0.3 to 0.7 mm or 0.4 to 0.6 mm. In effect, this part can be used to mimic the cornea of the human eye, which has a slight bulging profile.

In an embodiment, the retaining layer comprises, or consists of, a purse limiting means. In an embodiment, the retaining layer has a circular plate body region with a diameter of 1 to 60 mm, 30 to 50 mm, or 40 to 45 mm. In an embodiment, the retaining layer is 0.1 to 5 mm, 2 to 4 mm, or 2.5 to 3.5 mm thick. In an embodiment, the plate body has a bore through its centre on its anterior face, which has a diameter of 2 to 10 mm, 4 to 8 mm, or 5 to 7 mm. In an embodiment, on the posterior face, the plate body has a bowl-shaped structure of diameter 5 to 30 mm, 12 to 20 mm, 14 to 16 mm and a depth of 0.05 to 0.5 mm, 0.1 to 0.4 mm, or 0.15 to 0.3 mm. In an embodiment, the plate body region connects to a surrounding ring-shaped support plate by 1 to 10, 2 to 8, or 4 to 6 spaced bridges. In an embodiment, the bridges are 5 to 15 mm, 8 to 12 mm, or 9 to 11 mm long and 2 to 12 mm, 5 to 10 mm, or 6 to 8 mm wide. In an embodiment, the ring-shaped plate is a ring with an outer diameter of 60 to 120 mm, 70 to 100 mm, or 85 to 90 mm and an inner diameter of 50 to 80 mm, 55 to 75 mm, or 60 to 70 mm. In an embodiment, the retaining layer is made of 3D printed resin. In an embodiment, the ring-shaped plate has an aperture at its apex to receive a side-mounted fluid outlet. In effect, this part limits the degree the elastic layer can bulge under pressure, and in doing so how it mimics the shape of the cornea of the human eye.

In a second aspect of the invention, there is provided a kit of parts comprising an artificial eye assembly as defined in the first aspect, wherein the layers are provided as separate layers which may be reversibly, or non-reversibly, combined to form the assembly. A kit of parts, e.g. layers, allows a modular way in which to make artificial eye assemblies. This permits versatility in artificial eye design.

In a third aspect of the invention, there is provided a use of an artificial eye assembly as defined in the first aspect of the invention to study ocular drug kinetics.

In a fourth aspect of the invention, there is provided a method of studying ocular drug kinetics in an eye using an assembly as defined in the first aspect of the invention comprising:

(i) pumping fluid into the fluid inlet of the assembly;
(ii) establishing a steady state first flow rate out of the fluid outlet;
(iii) when present, establishing a steady state second flow rate out of the posterior outlet, and optionally adjusting the third flow rate of the balancing fluid, such that the sum of the second and third flow rates will be equal to the first flow rate;
(iv) injecting a drug into the assembly via the injection inlet;
(v) measuring the rate at which the drug exits the assembly via the fluid outlet;
(vi) when present, measuring the rate at which the drug exits the assembly via the posterior outlet;
(vii) optionally, adding a thermally regulated fluid to the volume to control the temperature of the assembly or part of the assembly;
(viii) optionally, rocking, agitating or twisting the assembly to simulate eye saccades, head movement, waking and sleeping cycles.

In an embodiment, the drug or active agent which may bind to one or more layers or parts of the layers are selected from any types of intravitreal proteins and peptides (e.g. but not limited to bevacizumab, ranibizumab, aflibercept, infliximab, brolucizumab), small molecules (e.g. but not limited to triamcinolone acetonide, dexamethasone, dexamethasone sodium phosphate, ganciclovir, vancomycin, foscarnet, cidofovir, fomvirsen, methotrexate, amikacin, amphotericin, voriconazole) and formulations thereof (e.g. encapsulating above drugs with polymers such as PLGA, PCL, NIPAAM, PVP, collagen, chitosan and hyaluronic acid).

The present invention will now be further described with reference to the following non-limiting examples and the accompanying illustrative drawings, of which:

BRIEF DESCRIPTION OF THE DRAWINGS

FIG. 3 shows a cross-sectional view taken through the assembly shown in FIG. 2.

FIG. 4a to 4c shows cross-sectional views of the posterior layer (10) shown in FIG. 1.

FIG. 5a to 5c shows cross-sectional views of the shaping layer (30) shown in FIG. 1.

Like parts and features have been given like reference numerals.

DETAILED DESCRIPTION OF THE INVENTION

Figure 1:
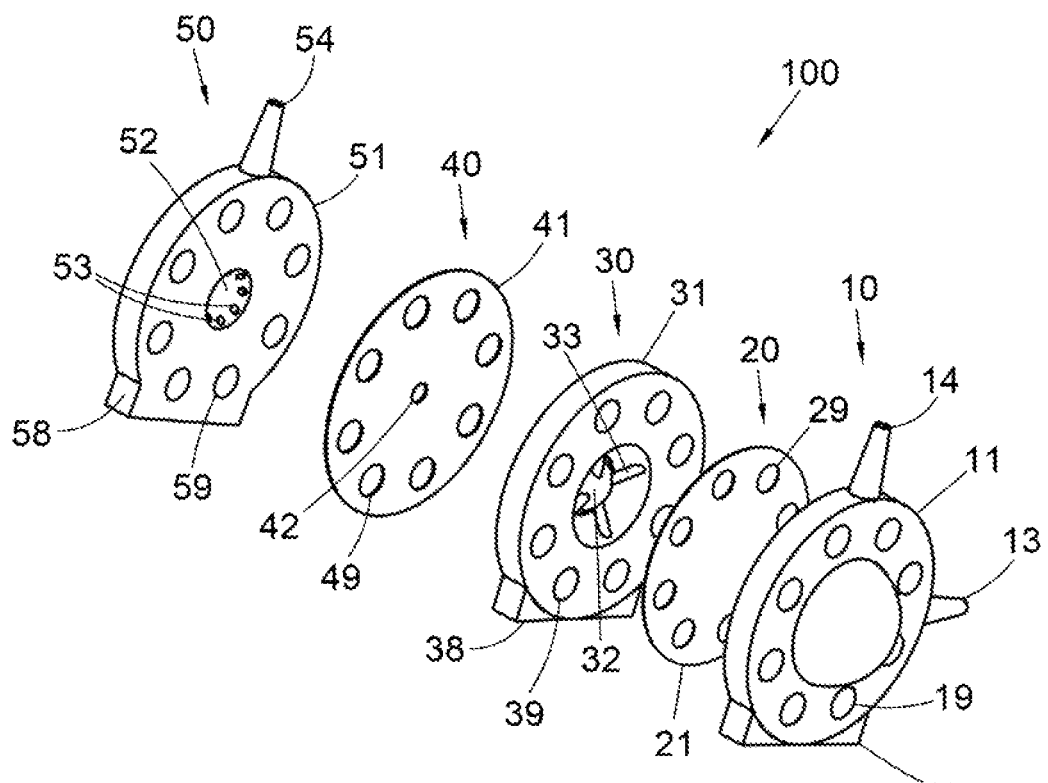
FIG. 1 shows an exploded perspective view of a first embodiment (100) of the invention.

FIG. 1 is an exploded perspective view of a first embodiment of the invention (100). The artificial eye assembly (100) comprises a posterior layer (10), a flow resistive layer (20), a shaping layer (30), a flow constricting layer (40), and an anterior layer (50).

The posterior layer (10) comprises a region that is shaped/dimensioned to mimic the back of the eye. The posterior layer (10) is made of 3D-printed resin. The posterior layer has a circular plate body region (11), which stands on a flattened base region (18). The circular plate region (11) has a diameter of 50 mm and is 6 mm thick at the base (18). The plate has a centrally located bowl-shape cavity region (12), which starts at the circular plate region. The bowl-shaped cavity (12) has an internal diameter of 22 mm and a depth of 14 mm. The bowl is 2 mm thick in the region where it extends from the plate. The posterior cavity (12) is fed by a side-mounted fluid inlet (13). Fluid may also be injected into the posterior cavity (12) via a top-mounted injection inlet (14). The side-mounted inlet (13), which is orthogonal to the top-mounted injection inlet (14), is 5 mm wide and tapers to 3 mm at its end and contains a 2 mm wide fluid conduit. The top-mounted inlet (14) is 5 mm wide and tapers to 3 mm at its end and contains a 2 mm wide fluid conduit. The body region (11) contains eight evenly spaced screw holes (19), the holes passing through the body (11). The screw holes have a diameter of 6.5 mm to accommodate M6 screws.

The flow resistive layer (20) is a thin disc (21) made of cellulose ester. It has a radius of 25 mm and is between 0.01 and 2 mm thick. The disc has a molecular weight cut off of 300 kDa. The body region (21) contains eight evenly spaced screw holes (29), the holes passing through the body (21). The screw holes have a diameter of 6.5 mm to accommodate M6 screws. In an alternative embodiment, the eight screw holes (29) can be omitted and the disc can be sandwiched in place.

The shaping layer (30) is made of 3D-printed resin. The shaping layer has a plate body region (31), which stands on a flattened base region (38). The plate region has a diameter of 50 mm and is 6 mm thick at the base (38). The plate has a bowl-shaped bore through its centre (i.e. second aperture), which has an internal diameter of 21 mm and a depth of 6 mm. Centrally located with respect to the bowl-shaped bore is a shaping structure (32), which is connected to the body (31) by four evenly spaced ribs/webs (33). The shaping structure (32) is broadly shaped/dimensioned to mimic the shape of a human lens. The shaping structure (32) has a radius of curvature for the anterior-facing surface of 10 mm and the radius of curvature for the posterior-facing surface of 6 mm, the apexes of the anterior-facing and posterior-facing surfaces being 9 mm apart. The body region (31) contains eight evenly spaced screw holes (39), the holes passing through the body (31). The screw holes have a diameter of 6.5 mm to accommodate M6 screws.

The flow constricting layer (40) contains a region broadly shaped/dimensioned to mimic the iris and pupil of the human eye. The flow constricting layer (40), is made of silicone. The flow constricting layer has a circular plate body region (41). The plate region has a diameter of 50 mm and is 0.4 mm thick. The plate has a bore through its centre (42), which has a diameter of 4 mm. The body region (41) contains eight evenly spaced screw holes (49), the holes passing through the body (41). The screw holes have a diameter of 6.5 mm to accommodate M6 screws.

Figure 2:
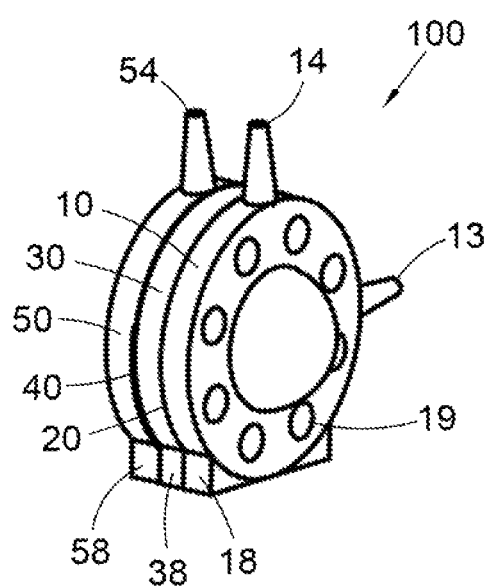
FIG. 2 shows a perspective view of the assembled embodiment shown in FIG. 1.

The anterior layer (50) contains a region broadly shaped/dimensioned to mimic the front of the eye. The anterior layer (50) is made of 3D-printed resin. The anterior layer has a circular plate body region (51), which stands on a flattened base region (58). The circular plate region has a diameter of 50 mm and is 6 mm thick at the base (58). The plate has a centrally located bowl-shape cavity region (52) within the circular plate region. The bowl-shaped cavity (52) has a diameter of 15.4 mm and a depth of 3 mm. The anterior cavity (52) connects to eight drainage holes (53) located in the plate body (51). The eight drainage holes (53) connect to a common torus-shaped drainage conduit in the plate body (51), which surrounds the anterior cavity. The common drainage conduit in turn connects to a top-mounted fluid outlet (54). The top-mounted fluid outlet (54) is 5 mm wide and tapers to 3 mm at its end and contains a 2 mm wide fluid conduit. The body region (51) contains eight evenly spaced screw holes (59), the holes passing through the body (51). The screw holes have a diameter of 6.5 mm to accommodate M6 screws. FIG. 2 shows a perspective view of the assembled embodiment shown in FIG. 1, and FIG. 3 shows a cross-sectional view taken through the assembly shown in FIG. 2.

In use, the layers shown in FIG. 1 are assembled by bringing the parts together and securing them in place in a fluid-tight manner with a maximum of eight M6 screws. That is, the posterior face of the anterior layer (50) is brought into contact with the anterior face of the flow constricting layer (40); the posterior face of the flow constricting layer (40) is brought into contact with the anterior face of the shaping layer (30); and the posterior face of the shaping layer (30) is brought into contact with the anterior face of the posterior layer (10), and in so doing the thin flow resistive layer (20) is sandwiched between the shaping layer (30) and the posterior layer (10). The screws pass through the aligned screw holes (19, 29, 39, 49 and 59). When assembled, the assembly rests on the base portions (18, 38 and 58). The flow resistive layer (20) is screwed in place by punching eight holes for the M6 screws, and is sandwiched between the posterior layer (10) and the shaping layer (30) to make it fluid tight. Optionally, a fluid permeable packing material, e.g. hyaluronic acid, is placed in the posterior cavity (12) either during or after assembly. Typically, in use, a fluid is pumped into the posterior cavity via the fluid inlet (13). The fluid passes through the various layers under pressure and is collected via the fluid outlet (54). In particular, pressure (e.g. 2-50 mmHg) is required to cause the fluid to pass through the pores in the flow resistive layer (20). Pressure also causes the movable flow resistive layer (20) onto/against the shaping body (32) of the shaping layer (30). In use, a drug containing fluid can be injected into the posterior cavity via the injection inlet (14). The top-mounted injection inlet (14) is closed by a valve. The fluid collected from the fluid outlet (54) is sent for analysis. For example, the drug can be monitored in real-time via a suitably calibrated UV, IR or MS sensor-based system. Alternatively, periodic samples can be gathered and analysed, e.g. by HPLC.

FIGS. 4a to 4c show cross-sectional views of the posterior layer (10) as shown in FIG. 1. FIG. 4a shows an anterior-facing cross-section of the posterior layer (10). FIG. 4b is a vertical section taken along A-A of FIG. 4a. FIG. 4c is a horizontal section taken along B-B of FIG. 4a. FIGS. 5a to 5c show cross-sectional views of the shaping layer (30) shown in FIG. 1. FIG. 5a shows an anterior-facing cross-section of the shaping layer (30). FIG. 5b is a vertical section taken along A-A of FIG. 5a. FIG. 5c shows a magnified central portion of FIG. 5a, in particular showing the shaping body (32) and the four connecting webs (33).

Figure 6:
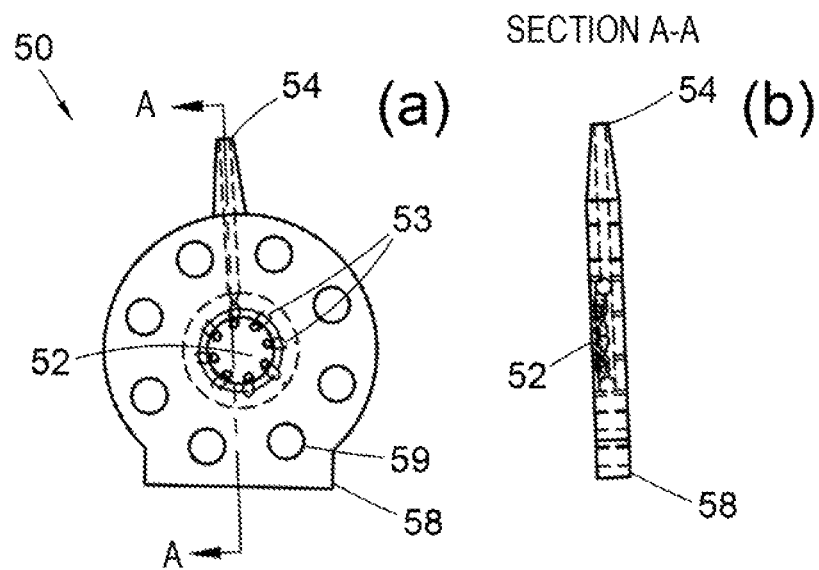
FIGS. 6a and 6b shows cross-sectional views of the anterior layer (50) shown in FIG. 1.

FIGS. 6a and 6b show cross-sectional views of the posterior layer (50) shown in FIG. 1. FIG. 6a shows a posterior-facing cross-section of the anterior layer (50). FIG. 5b is a vertical section taken along section A-A of FIG. 6a.

Figure 7:
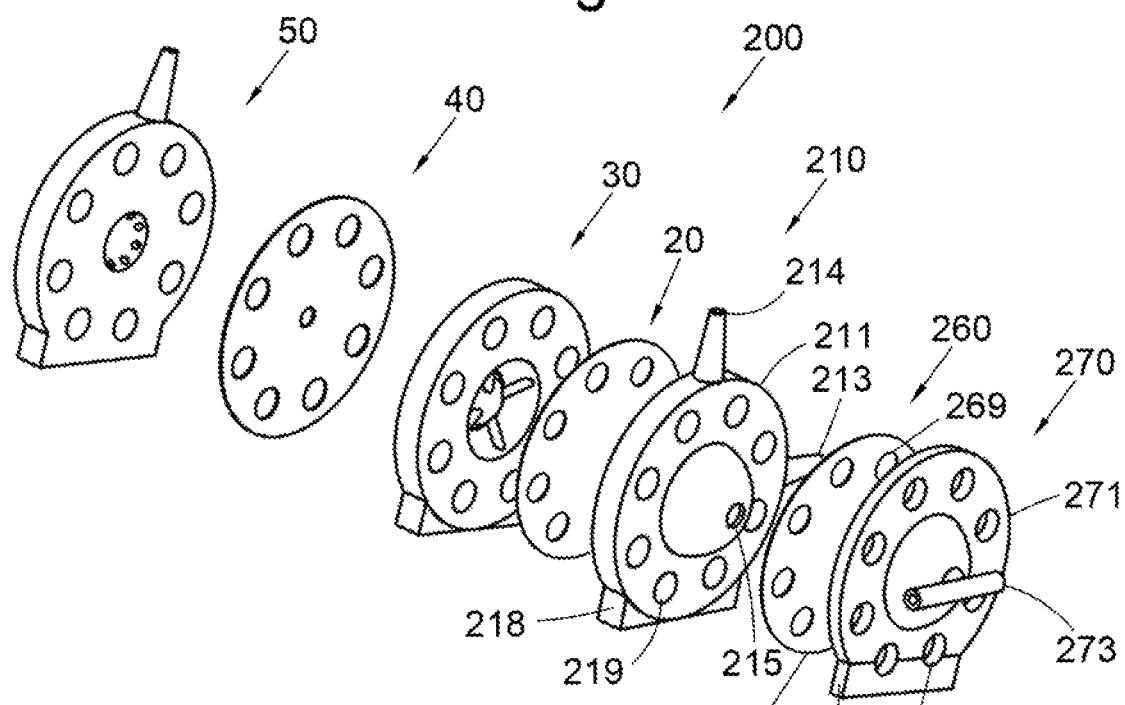
FIG. 7 shows an exploded perspective view of a second embodiment (200) of the invention.

FIG. 7 is an exploded perspective view of a second embodiment of the invention (200). The artificial eye assembly (200) comprises an outlet layer (270), second flow resistive layer (260), a posterior layer (210), a flow resistive layer (20), a shaping layer (30), a flow constricting layer (40), and an anterior layer (50).

The flow resistive layer (20), shaping layer (30), flow constricting layer (40), and the anterior layer (50) are substantially the same as described in FIGS. 1 to 6 above, and so are not further discussed here.

The posterior layer (210) comprises a region that is shaped/dimensioned to mimic the back of the eye. The posterior layer (210) is made of 3D-printed resin. The posterior layer has a circular plate body region (211), which stands on a flattened base region (218). The circular plate region has a diameter of 50 mm and is 6 mm thick at the base (218). The plate has a centrally located bowl-shape cavity region (212), which starts at the circular plate region. The bowl-shaped cavity (212) has a diameter of 22 mm and a depth of 15 mm (including the circular plate region). The bowl is 1 mm thick in the region where it extends from the plate. The posterior cavity has a centrally located cavity aperture (215) that passes through the bowl-shaped structure. The cavity aperture (215) has an aperture diameter of 5 mm. The posterior cavity (212) is fed by a side-mounted fluid inlet (213). Fluid may also be injected in to the posterior cavity (212) via a top-mounted injection inlet (214). The side-mounted inlet (213), which is orthogonal to the top-mounted injection inlet (214), is 5 mm wide and tapers to 3 mm at its end and contains a 2 mm wide fluid conduit. The top-mounted inlet (214) is 5 mm wide and tapers to 3 mm at its end and contains a 2 mm wide fluid conduit. The body region (211) contains eight evenly spaced screw holes (219), the holes passing through the body (211). The screw holes have a diameter of 6.5 mm to accommodate M6 screws.

The second flow resistive layer (260) is a thin disc made of reconstituted cellulose. It has a radius of 25 mm. The disc has a molecular weight cut off of 13 kDa. The body region (261) contains eight evenly spaced screw holes (269), the holes passing through the body (261). The screw holes have a diameter of 6.5 mm to accommodate M6 screws. In an alternative embodiment, the eight screw holes (269) can be omitted and the disc can be sandwiched in place.

The anterior face of the outlet layer (270) is broadly shaped/dimensioned to mate with the posterior face of the posterior layer (210). The outlet layer (270) is made of 3D-printed resin. The outlet layer (270) has a circular plate body region (271), which stands on a flattened base region (278). The circular plate region has a diameter of 50 mm and is 3 mm thick at the base (278). The plate has a centrally located bowl-shape mating cavity region (272), which starts at the circular plate region. The mating cavity (272) has a diameter of 24 mm and a depth of 9 mm. The wall of the mating cavity is 1 mm thick in the region where it extends from the plate. The mating cavity has a centrally located posterior outlet (275) that passes through the bowl-shaped structure. The posterior outlet (275) has substantially a funnel shape and feeds into the side of a substantially orthogonally arranged flow balancing conduit (273), the flow balancing conduit having an internal diameter of 2 mm. The body region (271) contains eight evenly spaced screw holes (279), the holes passing through the body (271). The screw holes have a diameter of 6.5 mm to accommodate M6 screws.

In use, the layers shown in FIG. 7 are assembled by bringing the parts together and securing them in place in a fluid-tight manner with eight M6 screws. The screws pass through the aligned screw holes (279, 269, 219, 39, 49 and 59). When assembled the assembly rests on base portions (278, 218, 38 and 58). The flow resistive layer (20) and second flow resistive layer (260) are screwed in place by punching eight holes for the M6 screws, and are sandwiched between adjacent layers to make it fluid tight. Optionally, a fluid permeable packing material e.g. hyaluronic acid, is placed in the posterior cavity (212) either during or after assembly. Typically, in use, a fluid is pumped into the posterior cavity via the fluid inlet (213). The fluid passes through the various layers under pressure and is collected via the fluid outlet (54). Pressure is required to cause the fluid to pass through the pores in the flow resistive layer (20). Pressure also causes the flow resistive layer (20) onto/against the shaping body (32) of the shaping layer (30). Pressure is also required to cause the fluid to pass through the pores in the second flow resistive layer (260). If the rate of flow through the second flow resistive layer is lower than the rate of flow through the first flow resistive layer, then fluid can be passed through the flow balancing conduit (273) to balance the rate of flows collected from the front (anterior) and back (posterior) of the eye assembly. In use, a drug containing fluid can be injected into the posterior cavity via the injection inlet (214). The fluid collected from the fluid outlet (54) and/or via the flow balancing conduit (273) are sent for analysis as discussed above with reference to the first embodiment (100).

FIGS. 8a to 8c show cross-sectional views of the posterior layer (210) shown in FIG. 7. FIG. 8a shows an anterior-facing cross-section of the posterior layer (210). FIG. 8b is a vertical section taken along A-A and FIG. 8c is a horizontal section taken along B-B of FIG. 8a.

FIGS. 9a to 9c show cross-sectional views of the outlet layer (270) shown in FIG. 7. FIG. 9a shows an anterior-facing cross-section of the outlet layer (270). FIG. 9b is a vertical section taken along A-A and FIG. 9c is a horizontal section taken along B-B of FIG. 9a.

Figure 10:
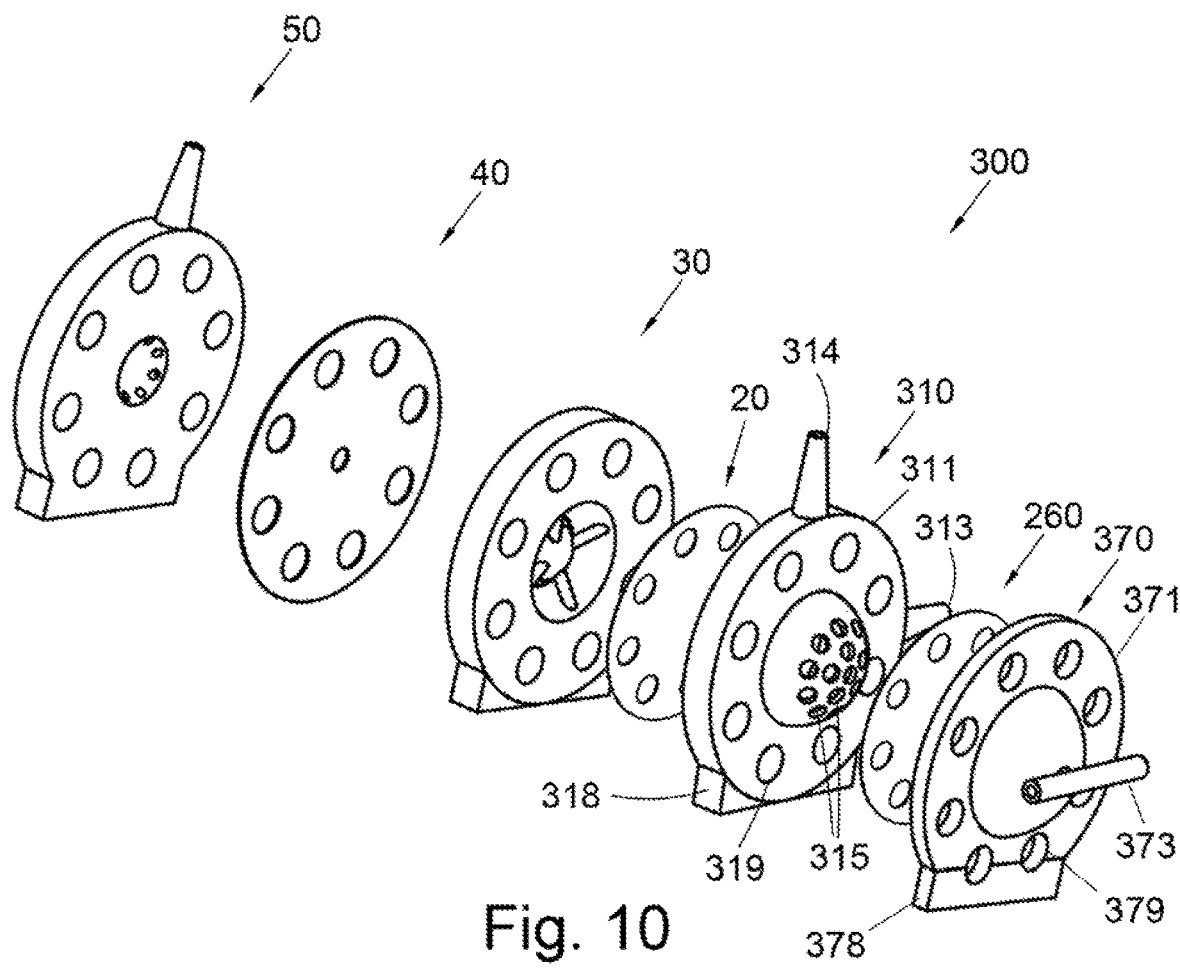
FIG. 10 shows an exploded perspective view of a third embodiment (300) of the invention.

FIG. 10 is an exploded perspective view of a third embodiment of the invention (300). The artificial eye assembly (300) comprises an outlet layer (370), second flow resistive layer (260), a posterior layer (310), a flow resistive layer (20), a shaping layer (30), a flow constricting layer (40), and an anterior layer (50). The posterior layer (310) has a circular plate body region (311), which stands on a flattened base region (318). Fluid may be injected via a top-mounted flow inlet (314) or a side-mounted flow inlet (313). The body region (311) contains eight evenly spaced screw holes (319), the holes passing through the body (311).

Figure 8:
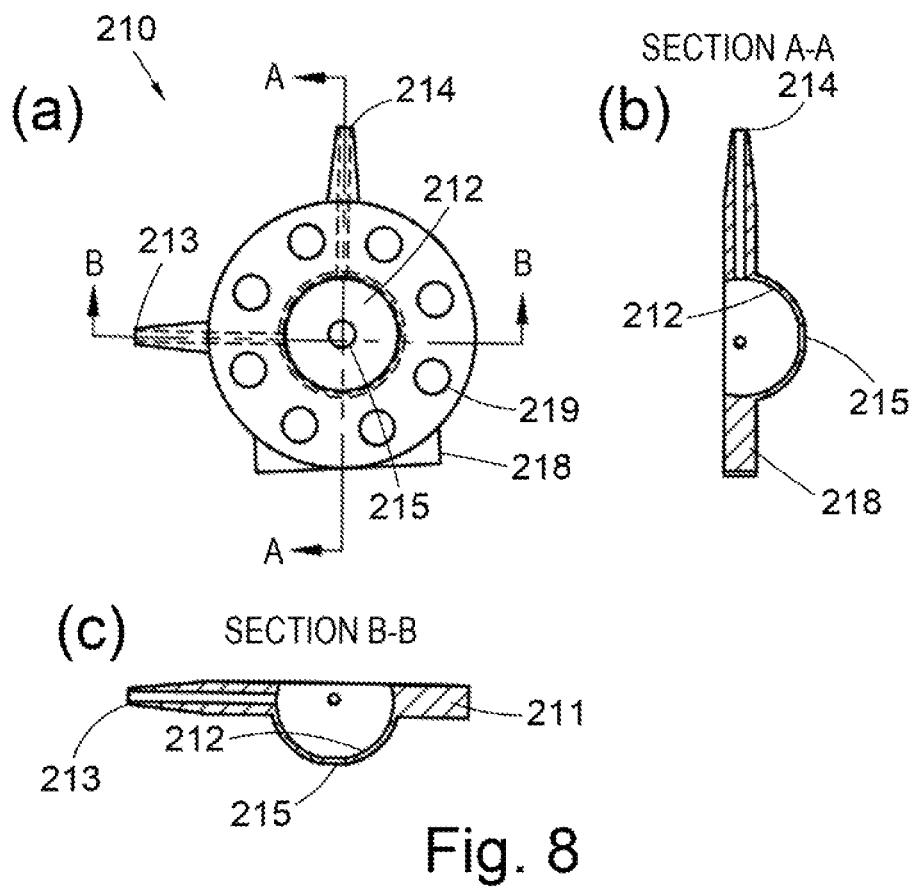
FIG. 8a to 8c shows cross-sectional views of the posterior layer (210) shown in FIG. 7.
Figure 9:
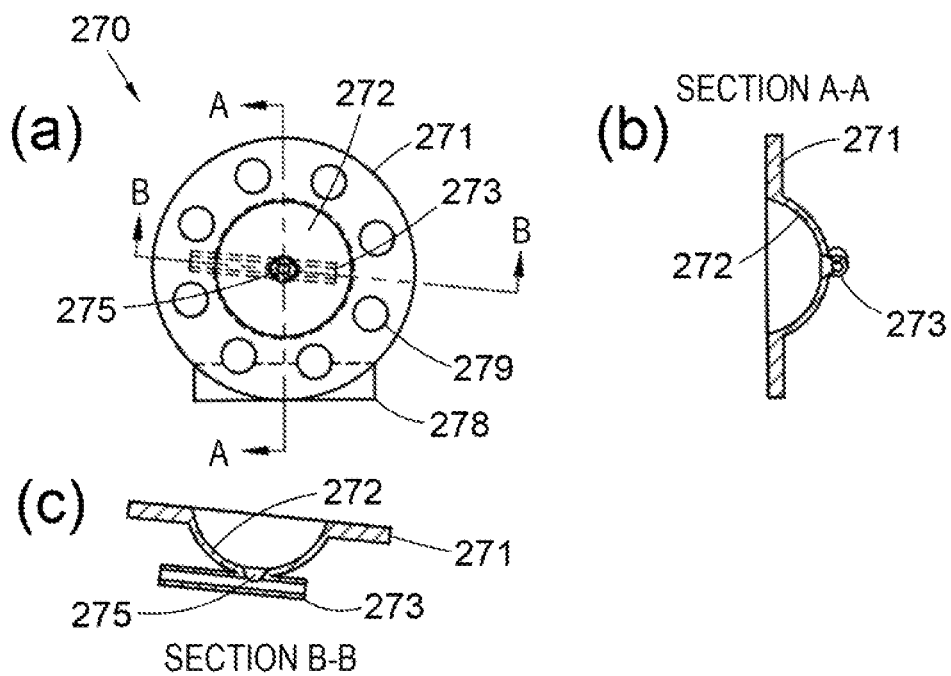
FIG. 9a to 9c shows cross-sectional views of the outlet layer (270) shown in FIG. 7.

The second flow resistive layer (260), flow resistive layer (20), shaping layer (30), flow constricting layer (40), and the anterior layer (50) are substantially the same as described in FIGS. 7 to 9 above, and so are not further discussed in detail here. The posterior layer (310) in the third embodiment (300) is substantially the same as the posterior layer (210) in the second embodiment (200) as shown in FIGS. 7 and 8. The substantive difference being that the centrally located cavity aperture (215) in the second embodiment (200) is replaced with a plethora (i.e. 26) of substantially evenly spaced apertures (315) in the third embodiment (300). As such, the bowl-shaped cavity (312) resembles the bowl region of a colander.

The outlet layer (370) in the third embodiment (300) is substantially the same as the outlet layer (270) in the second embodiment (200), as shown in FIGS. 7 and 9, and has a circular plate body region (371), which stands on a flattened base region (378). The body region (371) contains eight evenly spaced screw holes (379), the holes passing through the body (371). The substantive differences between the third embodiment (300) and the second embodiment (200) are that (i) the cavity region (372) is slightly bigger in the third embodiment (300) as compared to the cavity region (272) in the second embodiment (200). This is done to allow room for a fluid to pass through the plethora of holes (315) in the posterior layer (310); and (ii) and the flow balancing conduit (373) is shorter on one side as compared to the other.

In use, the third embodiment (300) is substantially assembled and used like the second embodiment (200) as described above. The exception being that fluid passes through a plethora of holes (315) in the posterior layer.

FIGS. 11a to 11c show cross-sectional views of the posterior layer (310) shown in FIG. 10. FIG. 11a shows a posterior-facing cross-section of the posterior layer (310). FIG. 11b is a vertical section taken along A-A of FIG. 11a. FIG. 11c is a horizontal section taken along B-B of FIG. 11a.

Figure 12:
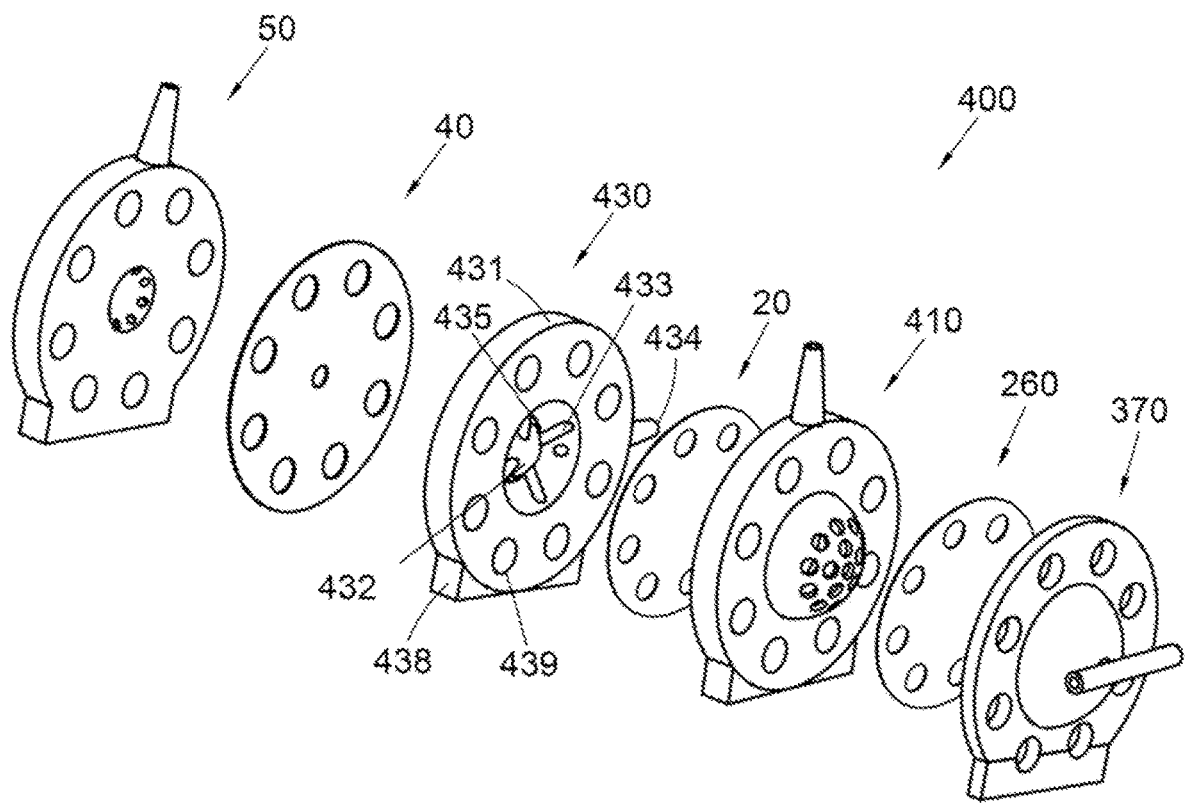
FIG. 12 shows an exploded perspective view of a fourth embodiment (400) of the invention.

FIG. 12 is an exploded perspective view of a fourth embodiment of the invention (400). The artificial eye assembly (400) comprises an outlet layer (370), second flow resistive layer (260), a posterior layer (410), a flow resistive layer (20), a shaping layer (430), a flow constricting layer (40), and an anterior layer (50).

Figure 11:
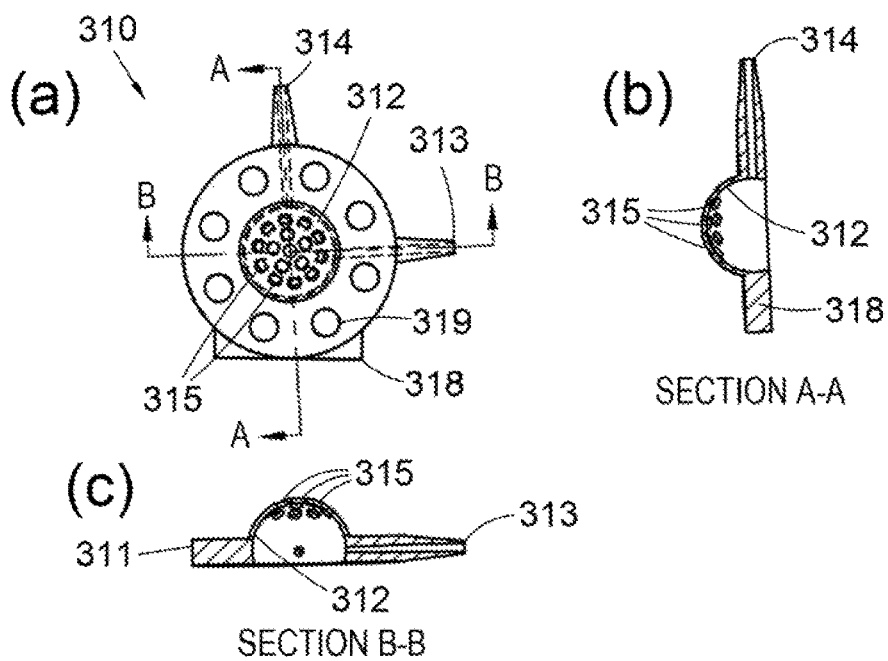
FIG. 11a to 11c shows cross-sectional views of the posterior layer (310) shown in FIG. 10.

The outlet layer (370), second flow resistive layer (260), flow resistive layer (20), flow constricting layer (40), and the anterior layer (50) are substantially the same as described in FIGS. 10 and 11 above, and so are not further discussed in detail here.

The posterior layer (410) in the fourth embodiment (400) is substantially the same as the posterior layer (310) in the third embodiment (300). The substantive difference is that there is no side-mounted flow inlet in the posterior layer (410) of the fourth embodiment (400), which would otherwise correspond to the side-mounted flow inlet (313) of the third embodiment (300).

The shaping layer (430) in the fourth embodiment (400) is substantially the same as the shaping layer (30) in the third embodiment (300), as shown in FIG. 10, and comprises a plate body region (431) which stands on a flattened base region (438). The body region (431) contains eight evenly spaced screw holes (439), the holes passing through the body (431). Centrally located with respect to the bowl-shaped bore is a shaping structure (432), which is connected to the body (431) by four evenly spaced ribs/webs (433). The substantive difference between the third embodiment (300) and the fourth embodiment (400) is that a side-mounted flow inlet (434) has been added, with the side-mounted flow inlet (434) feeding into the side of the central bowl-like bore (i.e. second aperture) 435. In effect, the substantive difference between the third embodiment (300) and the fourth embodiment (400), is that the side-mounted fluid inlet has been moved from the posterior layer to the shaping layer.

In use, the fourth embodiment (400) is substantively assembled and used like the third embodiment (300) as described above; with the exception that fluid enters the eye assembly at the shaping layer (430) and not at the posterior layer (410). If necessary, capillary tubing can be added at (or after) the fluid outlet (54), to generate a head of pressure, which would normally be generated by the flow resistive layer (20). If necessary, the collector reservoir can also be elevated to create a head of pressure.

Figure 13:
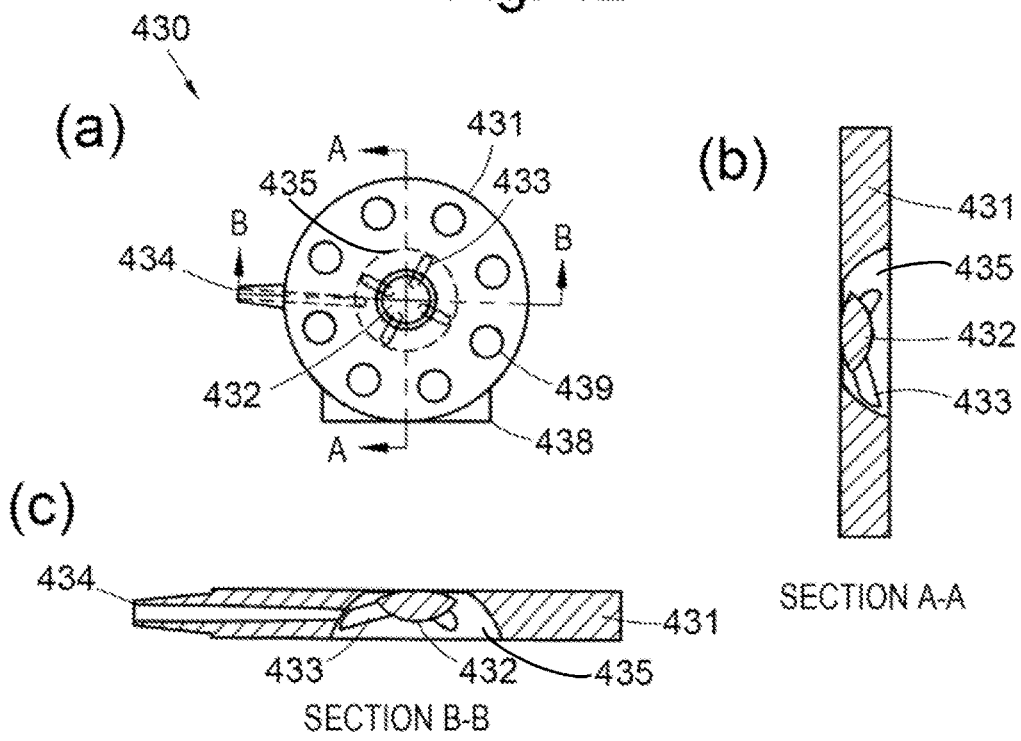
FIG. 13a to 13c shows cross-sectional views of the shaping layer (430) shown in FIG. 12.

FIGS. 13a to 13c show cross-sectional views of the shaping layer (430) shown in FIG. 12. FIG. 13a shows an anterior-facing cross-section of the posterior layer (430). FIG. 13b is a vertical section taken along A-A of FIG. 13a. FIG. 13c is a horizontal section taken along B-B of FIG. 13a.

Figure 14:
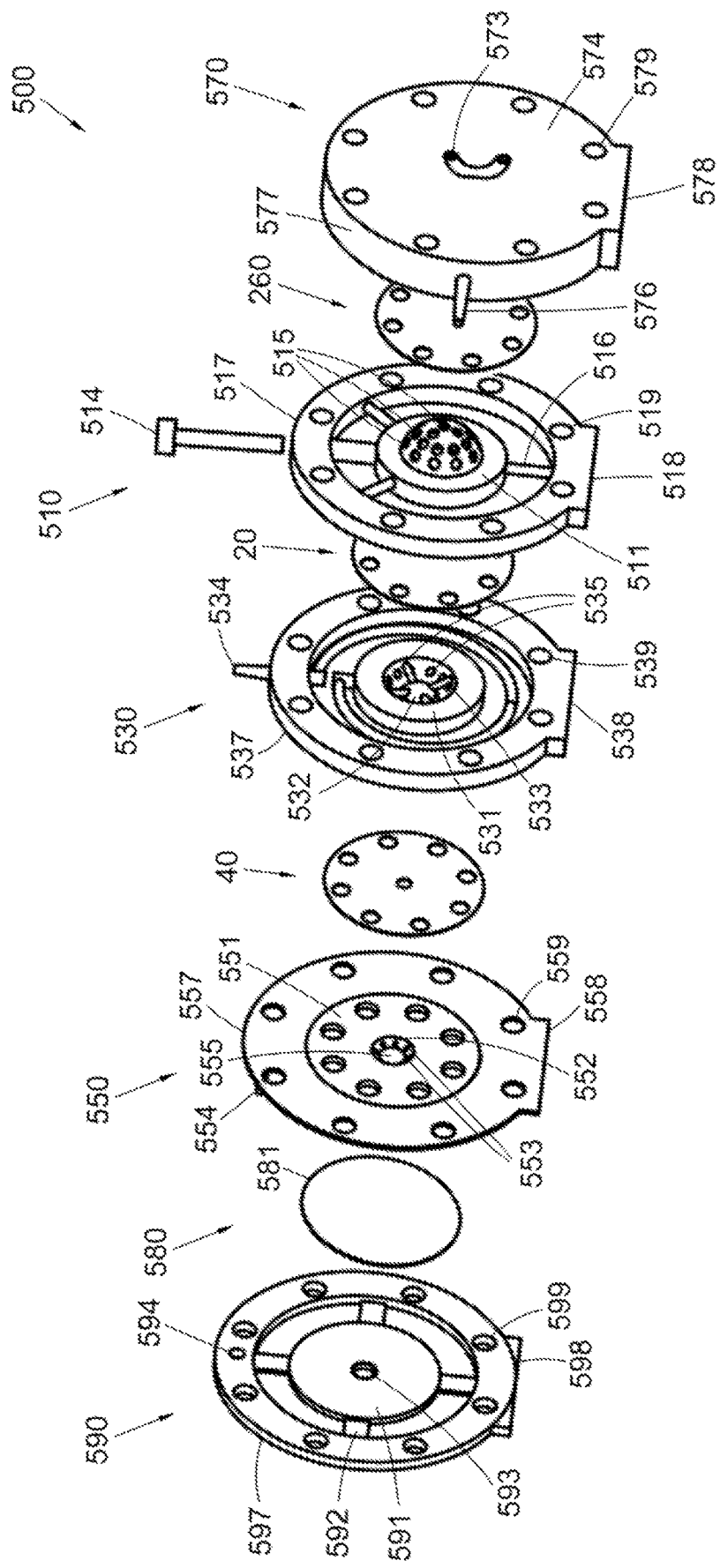
FIG. 14 shows an exploded perspective view of a fifth embodiment (500) of the invention.

FIG. 14 is an exploded perspective view of a fifth embodiment of the invention (500). The artificial eye assembly (500) comprises an outlet layer (570), second flow resistive layer (260), a posterior layer (510), a flow resistive layer (20), a shaping layer (530), a flow constricting layer (40), and an anterior layer (550), elastic layer (580) and a retaining layer (590).

The second flow resistive layer (260), flow resistive layer (20) and flow constricting layer (40) are substantially the same as described in FIG. 12 above, and so are not further discussed in detail here.

The anterior face of the outlet layer (570) is broadly shaped/dimensioned to mate with the posterior face of the posterior layer (510). The outlet layer (570) is made of 3D-printed resin.

The outlet layer (570) has a circular plate body region (571) and has a diameter of 37 mm and is 3 mm thick. The plate has a centrally located bowl-shaped mating cavity region (572), which starts at the circular plate region. The mating cavity (572) has a diameter of 26 mm and a depth of 7 mm. The bowl is 1.5 mm thick in the region where it extends from the plate body (571).

The plate body region (571) connects to a surrounding ring-shaped support plate (577) by three 13 mm long spaced apart ribs/webs. The ring-shaped support plate (577) is a ring with an outer diameter of 86 mm and an inner diameter of 64 mm and is 13 mm thick. The ring-shaped support plate (577) stands on a base region (578). The ring-shaped plate (577) contains eight evenly spaced screw holes (579), the holes passing through the body (577). The screw holes have a diameter of 6.5 mm to accommodate M6 screws. The posterior-facing surface of the support plate (577) is closed off by a thin sheet of 3D printed resin (574). The mating cavity (572) has a centrally located posterior outlet (575) that passes through the bowl-shaped structure and through the sheet of 3D printed resin (574). The posterior outlet (575) has substantially a funnel shape that feeds into the side of a substantially U-shaped vertically aligned flow balancing conduit (573); the flow balancing conduit having an internal diameter of 2 mm. The volume of space between the plate body region (571) and the ring-shaped plate (577) is fed by a side-mounted volume feed inlet (576), the volume feed inlet (576) is 4 mm wide and tapers to 2.5 mm at its end and contains a 2 mm wide fluid conduit.

The posterior layer (510) has a region that is broadly shaped/dimensioned to mimic the back of the eye. The posterior layer (510) is made of 3D printed resin. The posterior layer has a circular plate body region (511). The circular plate region has an external diameter of 37 mm and lowest internal diameter of 21 mm and is 6 mm thick. The plate has a centrally located bowl-shape cavity region (512), which starts at the circular plate region. The bowl-shaped cavity (512) has a diameter of 22 mm and a depth of 9 mm. The bowl is 1 mm thick in the region where it extends from the plate. The plate body region (511) connects to a surrounding ring-shaped support plate (517) by three 14 mm long spaced apart ribs/webs (516). The ring-shaped plate (517) is a ring with an outer diameter of 86 mm and an inner diameter of 64 mm and is 6 mm thick. The ring-shaped support plate (517) stands on a base region (518). The ring-shaped support plate (517) contains eight evenly spaced screw holes (519), the holes passing through the body (517). The screw holes have a diameter of 6.5 mm to accommodate M6 screws. The posterior cavity (512) has a plethora (i.e. 16) of substantially evenly spaced apertures (515) that pass through the bowl-shaped structure. As such, the bowl-shaped cavity (512) resembles the bowl region of a colander.

Fluid may be injected into the posterior cavity (512) via a top-mounted injection inlet (514), which has a fluid conduit that extends from outside of the ring-shaped support plate (517) into the cavity (512).

The injection inlet (514) contains a 5 mm wide fluid conduit.

The shaping layer (530) is made of 3D-printed resin. The shaping layer has a plate body region (531). The plate region has an external diameter of 37 mm and a lowest internal diameter of 21 mm and is 6 mm thick. The plate body region has a bowl shape through its centre, which has a diameter of 22 mm. Centrally located with respect to the bore is a shaping structure (532), which is connected to the plate body region (531) by four evenly spaced ribs/webs (533). The shaping structure (532) is broadly shaped/dimensioned to mimic the shape of a human lens. The shaping structure (532) has a radius of curvature for the anterior-facing surface of 10 mm and the radius of curvature for the posterior-facing surface of 6 mm, the apexes of the anterior-facing and posterior-facing surfaces being 9 mm apart.

The plate body region (531) connects to a surrounding ring-shaped support plate (537) via a spiralling fluid conduit. The ring-shaped plate (537) is a ring with an outer diameter of 86 mm and an inner diameter of 64 mm and is 6 mm thick. The ring-shaped support plate (537) stands on a base region (538). The ring-shaped plate (537) contains eight evenly spaced screw holes (539), the holes passing through the body (537). The screw holes have a diameter of 6.5 mm to accommodate M6 screws. The anterior-facing surface of the ring-shaped support plate (537) is closed off by a thin sheet of 3D-printed resin, except that it has a hole matching and corresponding to the bowl shape in the plate body region (531).

Fluid may enter the central bore of the plate body region (531) (adjacent to the shaping body (532)), via a top-mounted fluid inlet (534). The fluid conduit travels via a circuitous route to feed the central bowl-like bore of the plate body region (531). The conduit passes through the body of the ring-shaped plate (537), spirals before entering into the body of the plate body region (531). The conduit then bifurcates forming a square-shaped loop located within the plate body region (531). The square-shaped loop in turn has twelve spaced apart conduits (535) that feed into the central bore of the plate body region (531).

The anterior face of the ring-shaped plate (537) is equipped with eight evenly spaced peg-like protrusions (536), which cooperate with eight recesses (556) in the anterior layer (550), and pass through the eight holes (49) in the flow constricting layer (40).

The anterior layer (550) has a region broadly shaped/dimensioned to mimic the front of the eye. The anterior layer (550) is made of 3D-printed resin. The anterior layer has a circular plate body region (551) which stands on a flattened base region (558). The circular plate region has a diameter of 86 mm and is 1 mm thick at the base (558). The plate has a centrally located bowl-shape cavity region, the anterior cavity (552). The anterior cavity (552) has a diameter of 15.4 mm and a depth of 2.2 mm. The anterior cavity has a centrally located aperture (555), that passes through the bowl-shaped structure. The aperture (i.e. third aperture) has a diameter of 7.5 mm. The anterior cavity (552) has eight evenly spaced drainage holes (553), which connect to a torus-shaped drainage conduit (557) that surrounds the anterior cavity. This in turn connects to a second torus-shaped drainage conduit, which surrounds the first torus-shaped conduit. The second torus-shaped conduit in turn connects to a side-mounted fluid outlet (554), which is located at the apex of the circular body region (551). The fluid outlet (554) is 4 mm wide and tapers to 2.5 mm at its end, and contains a 2 mm wide fluid conduit. The body region (551) contains eight evenly spaced screw holes (559), the holes passing through the body (551). The screw holes have a diameter of 6.5 mm to accommodate M6 screws. As previously mentioned, the body region (551) contains eight recesses (556), which mate with projections (536) on the shaping layer (530).

The elastic layer (580) is a thin disc (581) made of clear silicone. It has a radius of 22 mm and is 0.5 mm thick with a Shore Hardness A.

The retaining layer (590) is made of 3D printed resin. The retaining layer has a circular plate body region (591). The plate region has a diameter of 44 mm and is 3 mm thick. The plate has a bore (593) through its centre on its anterior face. The bore (i.e. fourth aperture) has a diameter of 6.5 mm. On the posterior face, it has a bowl-shaped structure of diameter 15.4 mm and a depth of 0.2 mm. The plate body region (591) connects to a surrounding ring-shaped support plate (597) by four evenly spaced bridges (592). The bridges are 10.5 mm long and 7 mm wide. The ring-shaped plate (597) is a ring with an outer diameter of 86 mm and an inner diameter of 64 mm. The ring-shaped plate (597) has an aperture (594) at its apex to receive the side-mounted fluid outlet (554). The ring-shaped support plate (597) stands on a base region (598). The ring-shaped plate (597) contains eight evenly spaced screw holes (599), the holes passing through the body (597). The screw holes have a diameter of 6.5 mm to accommodate M6 screws.

In use, the layers shown in FIG. 14 are assembled by bringing the parts together and securing them in place in a fluid-tight manner with eight M6 screws. The screws pass through the aligned screw holes (579, 519, 539, 559 and 599). When assembled, the assembly rests on base portions (578, 518, 538, 558 and 598). The flow resistive layer (20), second flow resistive layer (260), flow constricting layer (40) and the elastic layer (580) are not screwed in place, but rather are sandwiched between adjacent layers. Optionally, a fluid permeable packing material e.g. hyaluronic acid, is placed in the posterior cavity (512), either during or after assembly. Typically, in use, a fluid is pumped into the bore of the shaping layer (530) via the fluid inlet (534). The fluid passes through the various layers under pressure and is collected via the fluid outlet (554). Pressure as well as diffusion is required to cause the fluid to pass through the pores in the flow resistive layer (20). Diffusion and pressure is required to cause the fluid to pass through the pores in the second flow resistive layer (260). If necessary, capillary tubing can be added at (or after) the fluid outlet (554) to generate a head of pressure. If the rate of flow out of the posterior outlet (575) is lower than the rate of flow through the fluid outlet (554), then fluid can be passed through the flow balancing conduit (573) to balance the rate of flows collected from the front (anterior) and back (posterior) of the eye assembly. In use a drug containing fluid can be injected into the posterior cavity via the injection inlet (514). The fluid collected from the fluid outlet (554) and/or via the flow balancing conduit (573) are sent for analysis as discussed above with reference to the first embodiment (100). In addition, a thermally regulated fluid can be introduced into the volume of space between the outlet layer (570) and shaping layer (530) via the volume feeding inlet (576). The thermally regulated fluid surrounds the circular plate body region (511) of the posterior layer (510) and surrounds the plate body region (531) of the shaping layer (inclusive of the spiralling fluid conduit of the shaping layer). In effect, in use, a gasket is created between the shaping layer (530) and the outlet layer (570), and so the volume of space created there within holds the thermally regulated fluid in a fluid tight manner.

Figure 15:
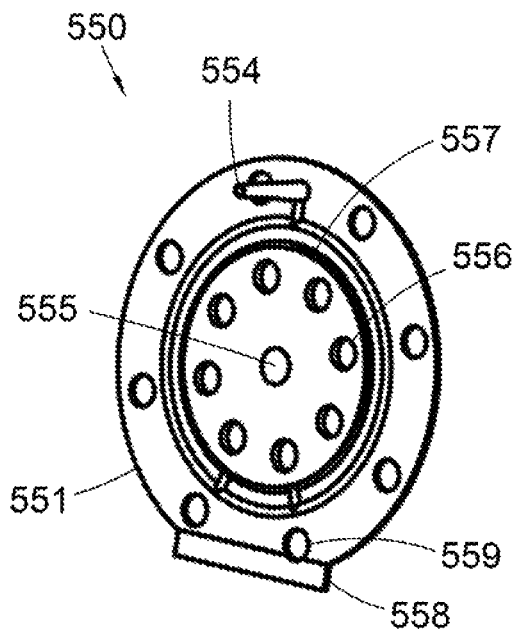
FIG. 15 shows the reverse face of the anterior layer (550) shown in FIG. 14.

FIG. 15 shows a perspective view of the anterior face of the anterior layer (550) as shown in FIG. 14. The side-mounted fluid outlet (554) can be seen more clearly from this view point.

Figure 16:
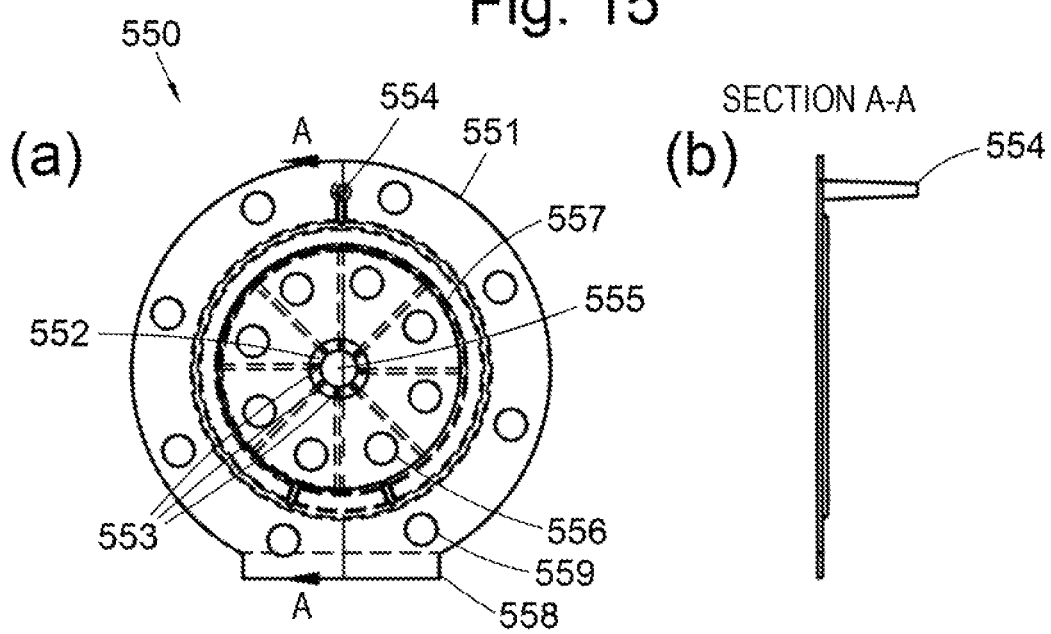
FIGS. 16a and 16b shows cross-sectional views of the anterior layer (550) shown in FIG. 14.

FIGS. 16*a* and 16*b* show cross-sectional views of the anterior layer (550) shown in FIG. 14. FIG. 16*a* shows a posterior-facing cross-section of the anterior layer (550). FIG. 16*b* is a vertical section taken along section A-A of FIG. 16*a*.

Figure 17:
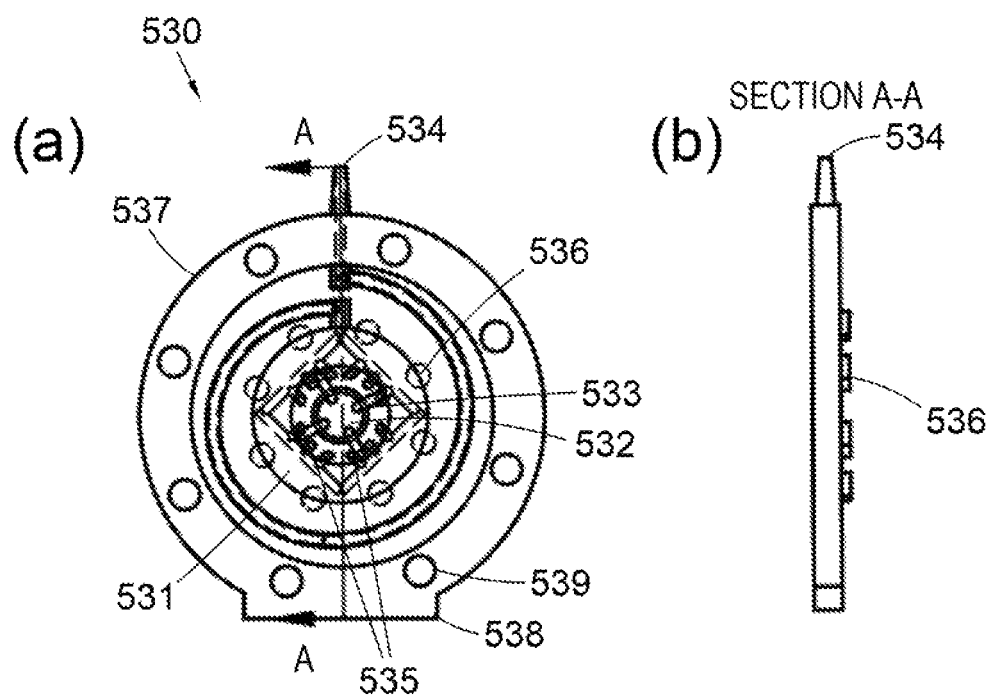
FIGS. 17a and 17b shows cross-sectional views of the shaping layer (530) shown in FIG. 14.

FIGS. 17*a* and 17*b* show cross-sectional views of the shaping layer (530) shown in FIG. 14. FIG. 17*a* shows a posterior-facing cross-section of the shaping layer (530). FIG. 15*b* is a vertical section taken along section A-A of FIG. 17*a*.

Figure 18:
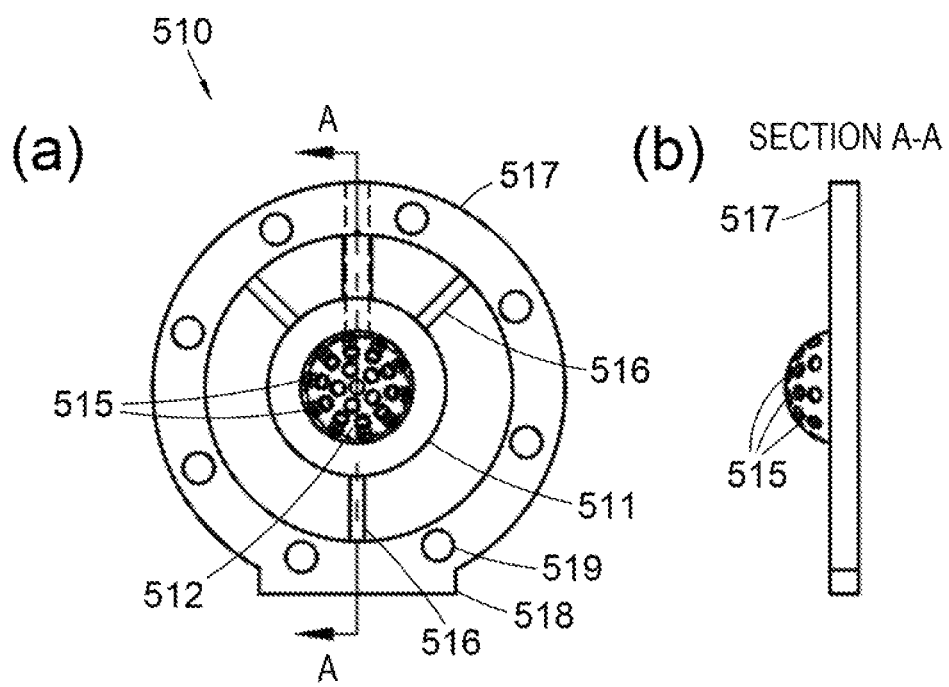
FIGS. 18a and 18b shows cross-sectional views of the posterior layer (510) shown in FIG. 14.

FIGS. 18*a* and 18*b* show cross-sectional views of the posterior layer (510) shown in FIG. 14. FIG. 18*a* shows a posterior-facing cross-section of the posterior layer (510). FIG. 18*b* is a vertical section taken along section A-A of FIG. 18*a*.

Figure 19:
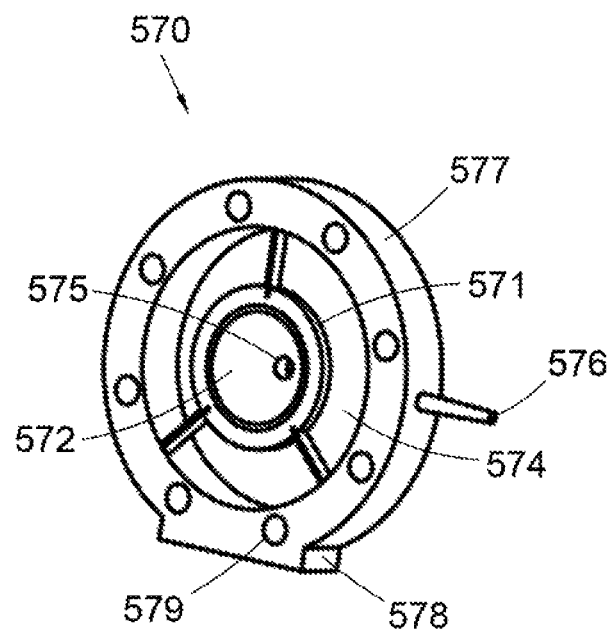
FIG. 19 shows the reverse face of the outlet layer (570) shown in FIG. 14.

FIG. 19 shows a perspective view of the anterior face of the outlet layer (570) shown in FIG. 14.

Figure 20:
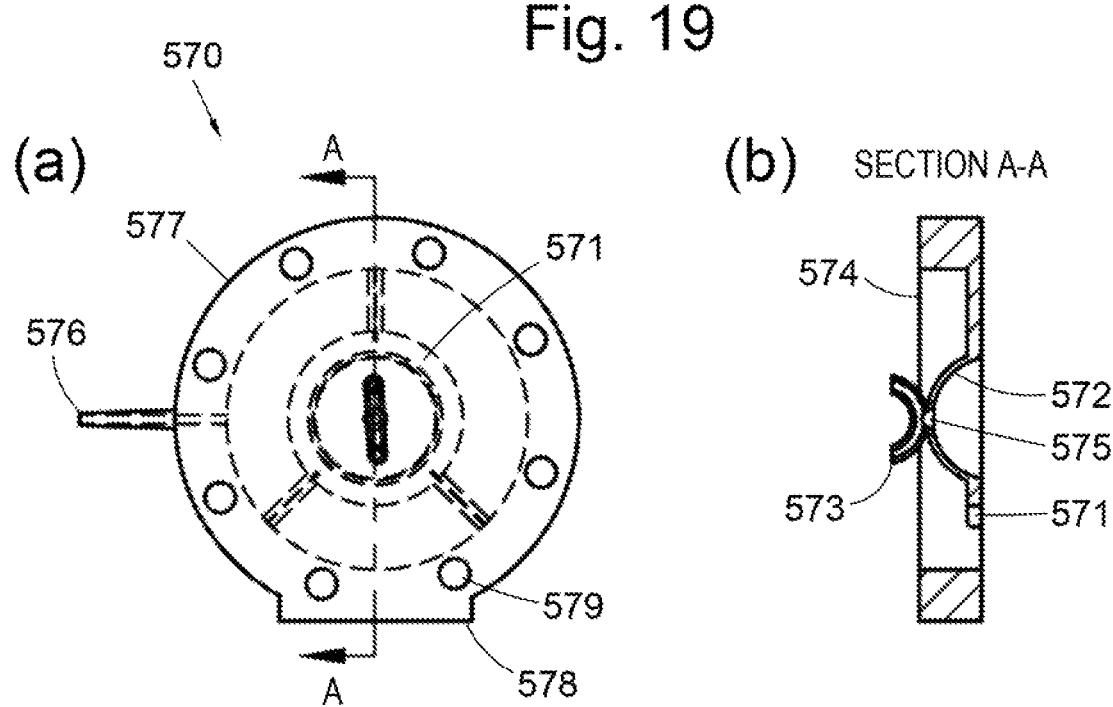
FIGS. 20a and 20b shows cross-sectional views of the outlet layer (570) shown in FIG. 14.

FIGS. 20*a* and 20*b* show cross-sectional views of the outlet layer (570) shown in FIG. 14. FIG. 20*a* shows a posterior-facing cross-section of the outlet layer (570). FIG. 20*b* is a vertical section taken along section A-A of FIG. 20*a*.

EXAMPLES

1. Method of Assembling an Eye Assembly Embodiment Comprising a Single Flow Restrictive Layer (e.g. See FIG. 1)

Preparing Membranes
Cut the membrane of the flow restrictive layer into a round shape with a 50 mm diameter.
Create eight holes in the membrane for the screws using a punch and hammer.

Assembly
Align along the holes the anterior layer, flow constricting layer, shaping layer, flow restrictive layer and the posterior layer.
Fix the 8×M6 screws in position along the holes.
Tighten the screws to assemble the eye assembly embodiment.

Filling
Fill the posterior cavity of the posterior layer with the fluid packing material (e.g. hyaluronic acid) using a syringe with a 29 G needle via the injection inlet.
Fill the anterior cavity of the anterior layer with buffer (PBS, pH 7.4, 0.05% sodium azide) using a syringe with a 29 G needle via the fluid outlet.
Connect capillary tubes (e.g. 1.0 mm ID) to the fluid inlet, injection inlet and fluid outlet.
Put a valve on the injection inlet and close it.

2. Method of Assembling an Eye Assembly Embodiment Comprising Two Flow Restrictive Layers (e.g. See FIG. 7)

Preparing Membranes
Prepare the membrane of the (first) flow restrictive layer and the membrane of the second flow restrictive layer as per Example 1.

Assembly
Align along the holes the anterior layer, flow constricting layer, shaping layer, (first) flow restrictive layer, posterior layer, second flow restrictive layer and outlet layer.
Fix the 8×M6 screws in position along the holes.
Tighten the screws to assemble the eye assembly embodiment.

Filling
Fill the posterior cavity and anterior cavity as described in Example 1 above.

3. Method of Assembling an Eye Assembly Comprising Two Flow Restrictive Layers, Elastic Layer and a Retaining Layer (e.g. See FIG. 14)

Preparing Membranes
Prepare the membrane of the (first) flow restrictive layer and the membrane of the second flow restrictive layer as per Example 1.

Assembly
Fix the membrane of the (first) flow restrictive layer between the shaping layer and the posterior layer.

When present, use the protrusions on the shaping layer to fix the flow constricting layer in place.

Fix the membrane of the second flow restrictive layer between the posterior layer and the outlet layer.

Align the 8×M6 screws in position along the anterior layer, flow constricting layer, shaping layer, posterior layer and outlet layer.

Place the anterior layer, elastic layer and retaining layer in turn on to the flow constricting layer.

Tighten the screws to assemble the eye assembly embodiment.

Filling the Eye Assembly with Filling Materials

Fill the posterior cavity and anterior cavity as described in Example 1 above.

4. Use of Eye Assembly

Eye Assembly

Assemble the eye assembly embodiment as described above in Examples 1 to 3, ensuring that it is fluid tight (i.e. it has no leaks).

Rocking Platform

If using the rocking platform, place the assembly on top of a rockable platform and secure the assembly to the platform.

External Temperature Control

If using a hot bath, fill the bath with distilled water and switch on the heating plate setting the temperature to 37° C. (or the desired temperature), and place the eye assembly embodiment in the bath. Allow the eye assembly embodiment to thermally equilibrate for 24 hours.

Internal Temperature Control

If using an internal temperature controlling system (e.g. an eye assembly embodiment with a gasket; e.g. see FIG. 14), connect the volume feed inlet to the column of water (i.e. the thermally regulated fluid) and place the eye assembly on a heating plate. Allow the thermally regulated fluid to enter into the volume of space between the outlet layer and shaping layer via the volume feeding inlet.

Pumping Fluids

Connect the fluid inlet to the microfluidic system. Connect the fluid outlet to a reservoir. If using a flow balancing conduit, connect a capillary tube (e.g. 1.0 mm ID) to the flow balancing conduit. Set the pump pressure, and allow to run at a fixed pressure for 24 hours at the selected temperature. If present, adjust the flow into the flow balancing conduit such that the rate of flow out of the flow balancing conduit matches the rate of flow coming out of the flow outlet.

Drug Delivery

Once the system has temperature and pressure equilibrated, usually allowing this to happen over 24 hours or more, inject the desired drug/formulation into the eye assembly embodiment via the injection inlet and then seal the valve.

Rocking Experiments

If using a rocking platform, turn on the rocking and launch the waking and sleeping cycle program.

Data Acquisition

After the drug has been administered, record the temperature, pressure, and the flow rate in, and flow rates out of the assembly, via the inlets and outlets, using the microfluidic and temperature software.

Collection of Samples

At designated times, collect samples from the outlets in collection vials, and store the vials in a freezer (−20° C.). Samples may then be analysed by the chosen assay, e.g. by high performance liquid chromatography (HPLC).

The invention claimed is:

1. An artificial eye assembly comprising: an anterior layer comprising an anterior cavity; a flow constricting layer comprising a first aperture, wherein the first aperture is in fluid communication with the anterior cavity; a shaping layer comprising a second aperture and a shaping structure, wherein the shaping structure is located within, partially within, or outside of the second aperture, and wherein the shaping structure comprises one or more webs, the webs connecting the structure to the rest of the shaping layer, wherein the second aperture is in fluid communication with the first aperture; a flow resistive layer comprising pores, wherein pores of the layer are in fluid communication with the second aperture; a posterior layer comprising a posterior cavity, wherein the posterior cavity is in fluid communication with pores of the flow resistive layer; a fluid inlet located in the anterior and/or posterior cavity, or located within or outside of the second aperture; a fluid outlet located in the anterior cavity; and an injection inlet located in the posterior cavity and/or located in the anterior cavity, wherein the anterior cavity and the posterior cavity are in fluid communication with one another via a fluid path formed through the layers; and wherein a fluid introduced under pressure into the assembly via the fluid inlet will flow along the fluid path and exit the assembly via the fluid outlet with a first flow rate.

2. The artificial eye assembly according to claim 1, wherein the posterior cavity comprises one or more cavity apertures, and the assembly further comprises: a second flow resistive layer comprising pores, wherein pores of the second flow resistive layer are in fluid communication with the one or more cavity apertures; an outlet layer comprising a posterior outlet, wherein the posterior outlet is in fluid communication with pores of the second flow resistive layer; and a flow balancing conduit in fluid communication with the posterior outlet, wherein the posterior cavity and the flow balancing conduit are in fluid communication with one another via a second fluid path, wherein the fluid introduced under pressure into the assembly via the fluid inlet will also flow along the second fluid path and exit the assembly via the posterior outlet with a second flow rate, and wherein a flow balancing fluid is configured to pass through the flow balancing conduit with a third flow rate, such that the sum of the second and third flow rates will be equal to the first flow rate.

3. The artificial eye assembly according to claim 1, wherein the anterior cavity comprises a third aperture and the assembly further comprises: an elastic layer sealing the third aperture; and a retaining layer configured to secure the elastic layer in place and which comprises a purse limiting means, wherein the fluid introduced under pressure into the assembly is configured to cause the elastic layer to purse, and wherein the purse limiting means limits the degree of pursing.

4. The artificial eye assembly according to claim 3, wherein the purse limiting means is a fourth aperture in the retaining layer, and wherein the elastic layer is sized to cover the fourth aperture.

5. The artificial eye assembly according to claim 1 wherein the assembly further comprises a temperature regulator configured to control or maintain the temperature within the assembly, or to induce a temperature difference within the assembly.

6. The artificial eye assembly according to claim 5, wherein the temperature regulating means comprises a volume for containing a thermally regulated fluid; and a heat or cooling means to adjust the temperature of the thermally regulated fluid, wherein the volume is in thermal contact with, and/or encompasses, one or more of: the outlet layer; the posterior layer; and the shaping layer, wherein the thermally regulated fluid is introduced into the volume and is maintained at a constant temperature, thereby transferring heat to, or from, the thermally contacted layers.

7. The artificial eye assembly according to claim 5, wherein the volume encompasses and/or extends through the outlet layer and the posterior layer, and abuts the shaping layer.

8. The artificial eye assembly according to claim 1, wherein, when the fluid inlet is located in, or adjacent to, the second aperture and the shaping layer is in thermal contact with the volume, the fluid passing through the inlet is arranged to flow in a circuitous fluid path through the shaping layer.

9. The artificial eye assembly according to claim 5 wherein the temperature regulating means causes thermal convection currents in a volume of fluid situated between the second aperture and the anterior cavity.

10. The artificial eye assembly according to claim 1, wherein the assembly further comprises a pump configured to pump the fluid under pressure through the assembly via the first fluid path and also via the second fluid path.

11. The artificial eye assembly according to claim 1, wherein a cavity volume between the flow resistive layer and the posterior cavity is filled with a fluid permeable packing material.

12. The artificial eye assembly according to claim 11, wherein the fluid permeable packing material is hyaluronic acid, collagen, agar, silicon oil, chitosan, alginates, or polysaccharides.

13. The artificial eye assembly according to claim 1, wherein one or more of the layers of the assembly are formed together as a single layer or 3D printed.

14. The artificial eye assembly according to claim 1, wherein the layers are modular units and may be combined to form the assembly.

15. The artificial eye assembly according to claim 2, wherein the posterior outlet is arranged orthogonally to the flow balancing conduit.

16. The artificial eye assembly according to claim 1, wherein the assembly further comprises a means to rock, twist, or agitate the assembly.

17. The artificial eye assembly according to claim 1, wherein the anterior cavity comprises a plurality of drainage holes in fluid communication with the fluid outlet.

18. The artificial eye assembly according to claim 1, wherein the flow constricting layer is capable of binding to a drug or active agent.

19. The artificial eye assembly according to claim 1, wherein the shaping layer is capable of binding to a drug or active agent.

20. The artificial eye assembly according to claim 1, wherein the second aperture comprises a plurality of inlet holes in fluid communication with the fluid inlet.

21. The artificial eye assembly according to claim 1, wherein the flow resistive layer comprises a membrane, the membrane comprising the pores.

22. The artificial eye assembly according to claim 21 wherein the membrane contacts the shaping structure and is shaped by the shaping structure.

23. The artificial eye assembly according to claim 2 wherein the second flow resistive layer comprises a second membrane, the second membrane comprising the pores.

24. The artificial eye assembly according to claim 2, wherein the flow rate permitted by the flow resistive layer is greater, equal, or less than the flow rate permitted by the second flow resistive layer.

25. The artificial eye assembly according to claim 3 wherein the elastic layer comprises, or consists of silicone.

26. A method of studying ocular drug kinetics in an eye using an assembly as defined in claim 1, the method comprising:
  (i) pumping fluid into the fluid inlet of the assembly;
  (ii) establishing a steady state first flow rate out of the fluid outlet;
  (iii) establishing a steady state second flow rate out of the posterior outlet and adjusting the third flow rate of the balancing fluid, such that the sum of the second and third flow rates will be equal to the first flow rate;
  (iv) injecting a drug into the assembly via the injection inlet;
  (v) measuring the rate at which the drug exits the assembly via the fluid outlet;
  (vi) when present, measuring the rate at which the drug exits the assembly via the posterior outlet;
  (vii) adding a thermally regulated fluid to the volume to control the temperature of the assembly or part of the assembly; and
  (viii) rocking, agitating or twisting the assembly.

* * * * *